(12) United States Patent
Shimbo et al.

(10) Patent No.: US 7,494,815 B2
(45) Date of Patent: Feb. 24, 2009

(54) METHOD AND APPARATUS FOR ANALYZING COMPOUNDS WITH AMINO GROUP

(75) Inventors: Kazutaka Shimbo, Kawasaki (JP); Takashi Ohnuki, Kawasaki (JP); Hiroshi Miyano, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/563,324

(22) Filed: Nov. 27, 2006

(65) Prior Publication Data

US 2007/0269899 A1 Nov. 22, 2007

Related U.S. Application Data

(63) Continuation of application No. PCT/JP2005/009618, filed on May 26, 2005.

(30) Foreign Application Priority Data

May 26, 2004 (JP) ............................. 2004-156714

(51) Int. Cl.
 *G01N 27/62* (2006.01)
 *G01N 30/72* (2006.01)
(52) U.S. Cl. .................... 436/89; 436/96; 436/173; 250/281; 422/70
(58) Field of Classification Search ............... 436/89, 436/96, 83, 173, 56; 210/198.2, 656; 530/409; 250/281; 422/70
See application file for complete search history.

(56) References Cited

U.S. PATENT DOCUMENTS 5,827,426 A 10/1998 Fujii et al.
7,148,069 B2 12/2006 Miyano et al.
2005/0079624 A1 4/2005 Miyano et al.
2006/0141630 A1 6/2006 Fujii et al.
2006/0286673 A1 12/2006 Miyano et al.
2007/0269899 A1 11/2007 Shimbo et al.

FOREIGN PATENT DOCUMENTS

| JP | 58-055754 | 4/1983 |
| JP | 64-044848 | 2/1989 |
| JP | 2002-71660 | 3/2002 |
| JP | 2002-243715 | 8/2002 |
| WO | 03/069328 | 8/2003 |

OTHER PUBLICATIONS

Fischer, J. E., et al., "The Effect of Normalization of Plasma Amino Acids on Hepatic Encephalopathy In Man," Surgery, vol. 80, No. 1, Jul. 1976, pp. 77-91.
Felig, P., et al., "Plasma Amino Acid Levels in Diabetic Ketoacidosis," Diabetes, vol. 19, No. 10, Oct. 1970, pp. 727-729.
Iwaki, K., et al., "Activated Carbamate Reagent as Chiral Derivatizing Agent for Liquid Chromatographic Optical Resolution of Enantiomeric Amino Compounds," Chromatographia, vol. 23, No. 12, Dec. 1987, pp. 899-902.
U.S. Appl. No. 11/563,324, filed Nov. 27, 2006, Shimbo et al.
U.S. Appl. No. 12/140,099, filed Jun. 16, 2008, Yamada et al.

*Primary Examiner*—Walter D Griffin
*Assistant Examiner*—Christine T Mui
(74) *Attorney, Agent, or Firm*—Oblon, Spivak, McClelland, Maier & Neustadt, P.C.

(57) ABSTRACT

The present invention provides a method and apparatus for analyzing compounds with amino group(s) contained in biological organisms. In this method, a compound with amino group(s) is derivatized and then the derivative of the compound with amino group(s) is eluted by liquid chromatography using a stepwise elution means on a concentration gradient. Subsequently, the derivative of the compound with amino group(s) eluted from the liquid chromatography is detected by mass spectrometry.

14 Claims, 29 Drawing Sheets

US 7,494,815 B2

METHOD AND APPARATUS FOR ANALYZING COMPOUNDS WITH AMINO GROUP

CROSS-REFERENCE TO RELATED APPLICATIONS

The present application is a continuation of PCT/JP05/009618, filed on May 26, 2005, which claims priority to Japanese Application No. JP 2004-156714, filed on May 26, 2004, which are hereby incorporated by reference in their entirety.

BACKGROUND OF THE INVENTION

1. Field of the Invention

The present invention provides a method for analyzing compounds with amino groups (e.g., amino acids, peptides, and amino acid analogues) rapidly and easily with higher sensitivity by liquid chromatography/mass spectrometry (LS/MS), as well as an apparatus therefor.

2. Discussion of the Background

Amino acids in biological organisms are useful for the discriminative determination of diseases, including diseases associated with abnormalities in the amino acid metabolism. Amino acids are used, for example, for the diagnosis of congenital aminoacidopathy, for the indicator of severity determination or therapeutic treatment of liver disfunction, and for the understanding of the conditions of patients at a state of malnutrition.

As the most famous example thereof, the synthesis of valine, leucine and isoleucine, referred to as branched-chain amino acids (BCAA), is reduced in severe liver diseases such as fulminant hepatitis and liver impairment. Since phenylalanine, an aromatic amino acid (AAA), is metabolized mainly in liver, the blood concentration thereof is increased when the metabolism of phenylalanine is inhibited. Consequently, the concentration ratio of BCAA to AAA is reduced to a smaller value, and the level reflects the severity of liver diseases. The ratio BCAA/AAA is generally called Fisher ratio and has been traditionally used for the determination of liver disease severity (see, for example, Fisher J E, et al., "Surgery", 1976, July, Vol. 80, p. 77-91). Additionally, it is known that diabetes mellitus involves the increase of phenylalanine, tyrosine, isoleucine, leucine and valine and the decrease of alanine (see, for example, Felig P, et al., "Diabetes", 1970, October, Vol. 19, p. 727-728).

With respect to methods for analyzing amino acids, amino acid analyzers based on post-column derivatization are frequently used. According to the methods, generally, amino acids are separated on a cation exchange column, followed by color reaction with ninhydrin. However, the methods have a drawback of long analytical time. Recently, the analytical time of a standard analytical method for analytes of about 20 kinds of amino acids as protein hydrolysates is approximately 20 minutes due to the modifications of separation columns, buffer flow and the like (see, for example, official gazette of JP-A-2002-243715). Meanwhile, methods for analyzing amino acids on the basis of pre-column derivatization reaction are significantly studied. Any amino acid composing protein can be analyzed in about 4.5 minutes by a pre-column derivatization reaction process using phenylisothiocyanate as a reagent. By the LC-MS method using an analytical reagent developed by the present inventors, additionally, 20 kinds of amino acids are possibly analyzed in 2.8 minutes, as described (see, for example, Pamphlet of International Publication WO 03/069328). However, leucine and isoleucine are not separated from each other in this example. Therefore, leucine and isoleucine cannot be individually analyzed simultaneously.

Not only amino acids that compose proteins, but also a great number of amino acid analogues exist in biological organisms. Typically, the amino acid analogues include, for example, taurine, O-phosphoethanol amine, hydroxyproline, methionine sulfoxide, sarcosine, α-aminoadipic acid, citrulline, α-amino-n-butyric acid, pipecolic acid, homocysteine, homocitrulline, alloisoleucine, saccharopine, cystathionine, argininosuccinic acid, cysteine-homocysteine, β-alanine, aminolevulinic acid, β-aminoisobutyric acid (β-AiBA), γ-amino-n-butyric acid (GABA), homocystine (Hcys2), argininosuccinate anhydride, hydroxylysine, aminoethylcysteine, ornithine, 1-methylhistidine, and 3-methylhistidine. Various physiological functions are going to be discovered or elucidated in these amino acid analogues contained in biological fluids.

According to an analytical method on the principle of post-column derivatization, comprising separating amino acids and amino acid analogues (these are collectively referred to as compounds with amino group) on a cation exchange column and subsequent color reaction with ninhydrin, the analytical time for these 41 components of compounds with amino groups is 60 minutes at minimum; and the analytical time for 53 components is 148 minutes at minimum. (See, for example, official gazette of JP-A-2002-71660). Such a long analytical time is a serious factor disturbing research in regard to the physiological functions of amino acids. Even when a novel discovery into the relationship between amino acids and health or diseases is found, the information cannot effectively be employed due to processing delays and deficiencies in processing ability.

SUMMARY OF THE INVENTION

It is an object of the present invention to provide a method for analyzing compounds with amino groups including numerous kinds of amino acids and derivatives thereof, and amino acid analogues in biological organisms, far more rapidly, in a simpler manner, and at a higher sensitivity compared with methods available heretofore. It is also an object of the present invention to provide an apparatus for the implementation of the methods of the present invention.

For solving the problems existing in the art, the present inventors made various modifications of the LC/MS method for analyzing compounds with amino group. Specifically, the inventors found that numerous kinds of compounds with amino group could be analyzed simultaneously rapidly and in a simple manner at a high sensitivity, by preliminarily separating and eluting by liquid chromatography plural compounds with an amino group, of which the separation and detection involve difficulty by mass spectrometry because the masses thereof are identical, and continuously separating and detecting such compounds by mass spectrometry. Thus, the invention has been achieved.

Thus, the invention provides a method for analyzing compounds with an amino group by reacting a compound with an amino group, found in a sample containing the compound with amino group, with a reagent for derivatization to generate a derivative of the compound with amino group as represented by the following formula (I), eluting the derivative of the compound with amino group by liquid chromatography using a stepwise elution means on a concentration gradient, and detecting the derivative of the compound with amino group as eluted by the liquid chromatography, by mass spectrometry.

In this method, the following is the compound of formula (I)

In this formula, $Ar_1$ denotes an optionally substituted hydrocarbon, or a substituent containing a carbocyclic or a heterocyclic ring having an aromaticity; $R_1$ denotes a hydrogen atom, an optionally substituted alkyl group, or a saturated or unsaturated alkyl group which may or may not have a substituent; $R_2$ denotes an optionally substituted alkyl group; $Ar_1$ together with $R_1$ or $R_1$ together with $R_2$ may form a ring.

In another embodiment of the present invention is an apparatus for analyzing compounds with an amino group, comprising a reaction part for reacting a compound with amino group in a sample with a reagent for derivatization to generate a derivative of the compound with amino group as represented by the above described formula (I), a chromatography part for eluting the derivative of the compound with amino group, and a mass spectrometry part for detecting the derivative of the compound with amino group contained in the eluted solution from the chromatography part.

Other preferable modes for carrying out the invention are described in greater detail below.

By the method of the invention, about 40 kinds of typical compounds with amino group in biological organisms can be analyzed for a short time, for example, within 10 minutes. By the method, therefore, the analytical time can greatly be shortened, compared with amino acid analyzers in the related art. It was difficult in the related art to simultaneously analyze amino acids with the same mass, such as leucine and isoleucine by mass spectrometry alone. By the method of the invention, however, 100 kinds or more of compounds with amino acid including these biological amino acids can simultaneously be analyzed for an extremely short time.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

DESCRIPTION OF REFERENCE NUMERAL AND SIGNS USED IN THE FOREGOING FIGURES

Figure 1:
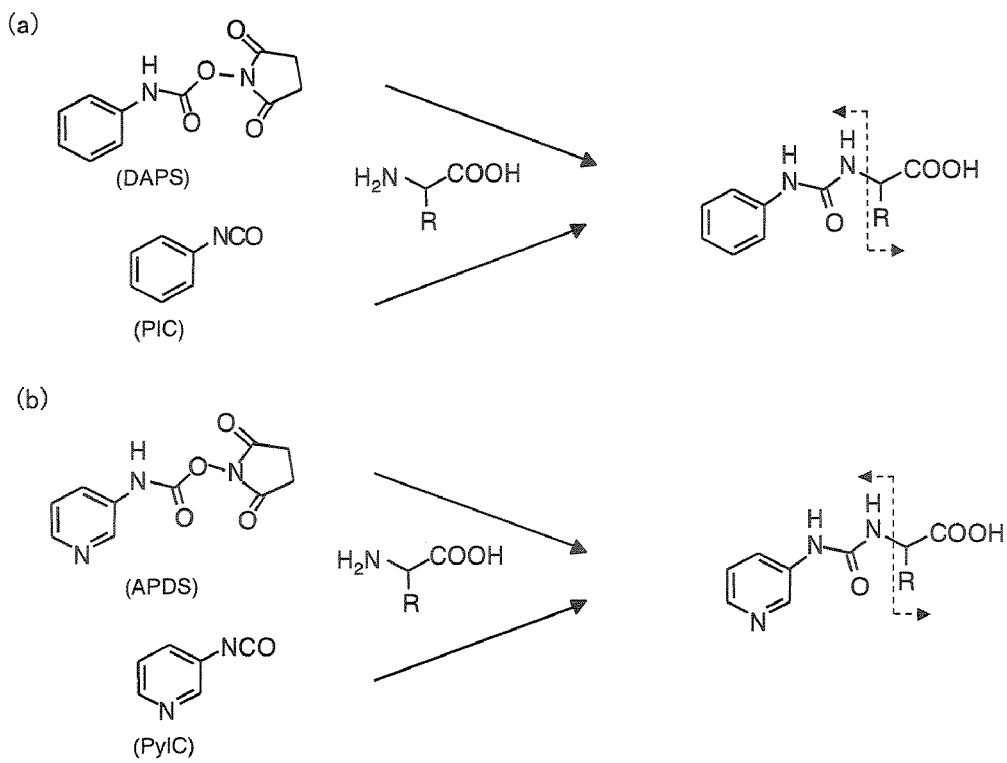
FIG. 1 shows a typical reaction scheme for generating a derivative of a compound with amino group, according to the method of the invention.

| | |
|---|---|
| 10 | Reaction part |
| 20 | Chromatography part |
| 21 | Separation column |
| 22 | Injection valve |
| 23a, 23b | Pump |
| 24a, 24b | Eluent |

DETAILED DESCRIPTION OF THE INVENTION

Unless specifically defined, all technical and scientific terms used herein have the same meaning as commonly understood by a skilled artisan in enzymology, chemistry, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In accordance with the invention, the term "compound with amino group" or "compound with an amino group" means a compound with primary amine and/or secondary amine within the molecule (which may be in a salt form). In this context, the primary amine and secondary amine may be present singly or in a plural number. Additionally, the compound with amino group existing in a sample may be of a single type or of a mixture of plural kinds. The compound with amino group includes, for example, amines (primary amine, secondary amine, and the like), amino acid, peptide, protein, polyamine and the like. Specifically, the compound with amino group includes those shown below in Table 1. The compound may contain plural kinds of such compounds. For example, the compound includes a mixture of plural kinds of amino acids, a mixture of one or more kinds of amino acids and one or more kinds of peptides, a mixture of one or more kinds of amino acids and one or more kinds of amines.

TABLE 1

| | | | |
|---|---|---|---|
| asparagines (Asn) | galactosamine (GalNH$_2$) | taurine (Tau) | putrescine (Put) |
| aspartic acid (Asp) | carnosine (Car) | tyramine (TyrNH$_2$) | proline(Pro) |
| O-acetylserine (O-AcSer) | kynurenine (Kyn) | tyrosine (Tyr) | prolinamide (ProAmide) |
| Nα-acetyllysine (Nα-AcLys) | glycine (Gly) | theanine (The) | S-benzil cysteine (BnCysH) |
| S-adenosylhomocysteine (AdHoCysH) | reduced glutathione (GSH) | tryptamine (TrpNH$_2$) | O-phosphoethanolamine (PEA) |
| S-aminoethyl cysteine (AECysH) | oxidized glutathione (GSSG) | tryptophan(Trp) | homoarginine(HoArg) |
| ε-amino-n-caproic acid (ε-ACA) | glutamine (Gln) | Nε, Nε, Nε-trimethyllysine (TMeLys) | homocarnosine (HoCar) |
| α-amino adipic acid (α-AAA) | glutamic acid (Glu) | norepinephrine (norEpi) | homocystine (HoCys$_2$) |
| 4-aminobenzoic acid (4-ABzA) | saccharopine (Saccha) | norvaline (norVal) | homocysteine (HoCysH) |
| α-aminoisobutyric acid (α-AiBA) | sarcosine(Sar) | norleucine(norLeu) | homocitrulline(HoCit) |
| β-aminoisobutyric acid (β-AiBA) | β-cyanoalanine (β-CNAla) | valine (Val) | homoserine (HoSer) |
| 5-aminovaleric acid (5-AVA) | α,ε-diaminopimelic acid (DAP) | histamine (HisNH$_2$) | homolanthionine (HoLan) |
| α-aminopimelic acid (α-APA) | 1,5-diaminopentane (1,5DApen) | histidinol (HisOH) | homoleucine (HoLeu) |
| α-amino-n-butyric acid (α-ABA) | α,γ-diaminobutyric acid (DABA) | histidine (His) | methionine (Met) |
| β-amino-n-butyric acid (β-ABA) | djenkolic acid (Dje) | β-hydroxyaspartic acid (β-HyAsp) | methionine sulphoxide (MetSOX) |
| γ-amino-n-butyric acid (GABA) | cystathionine (Cysthi) | 3-hydroxy anthranilic acid (3-HyAnth) | methionine sulfone (MetSulfone) |
| β-alanine (β-Ala) | cystamine (DTEA) | 3-hydroxykynurenine (3-HyKyn) | β-N-methylamino alanine (β-MeNH$_2$Ala) |
| alanine (Ala) | cystine (Cys$_2$) | hydroxy tyramine (HyTyr) | methylamine (MeNH$_2$) |
| argininosuccinic acid (ASA) | cysteamine (EtSHNH$_2$) | 5-hydroxytryptamine (5HT) | 1-methylhistamine (1MeHisNH$_2$) |

TABLE 1-continued

| | | | |
|---|---|---|---|
| arginine (Arg) | cysteine (CysH) | 5-hydroxytryptophan (5-HyTrp) | 1-methylhistidine (1MeHis) |
| anserine (Ans) | cysteic acid (CysA) | hydroxyproline (HyPro) | 3-methylhistidine (3MeHis) |
| anthranilic acid (Anth) | cysteine sulfinic acid (CSA) | hydroxylysine (HyLys) | monomethyl ethanolamine (MeEtOHNH)) |
| isoleucine (Ile) | citrulline (Cit) | pipecolic acid (Pip) | lanthionine (Lan) |
| Ethanolamine (EtOHNH$_2$) | dihydroxy-phenylalanine (DOPA) | hypotaurine (HypoTau) | lysine(Lys) |
| ethionine (Ethi) | dimethylamine (Me$_2$NH) | phenylalanine (Phe) | leucine (Leu) |
| epinephrine(Epi) | threonine(Thr) | 2-phenylethylamine (PheEtNH$_2$) | |
| ornithine (Orn) | serine (Ser) | phenylglycine (PhGly) | |

The term "reagent for derivatization" means a reagent for reaction with the compound with amino group to generate a derivative of the compound with amino group, as represented by the following formula (I).

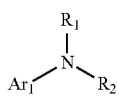
(I)

In formula (I), Ar$_1$ denotes an optionally substituted hydrocarbon, or a substituent containing a carbocyclic or a heterocyclic ring having an aromaticity; R$_1$ denotes a hydrogen atom, an optionally substituted alkyl group, or a ring forming carbon atom; R$_2$ represents an optionally substituted alkyl group; and Ar$_1$ together with R$_1$ or R$_1$ together with R$_2$ may form a ring.

In formula (I), the binding of Ar$_1$ to nitrogen atom may be the binding of a carbon ring or heterocyclic ring having an aromaticity directly to nitrogen atom and may additionally be the binding thereof via carbonyl group (—CO—), amide group (—NHCO—) and the like to nitrogen atom. Otherwise, the nitrogen atom may compose a part of a carbon ring or heterocyclic ring. The structure of such derivative of the compound with amino group includes for example:

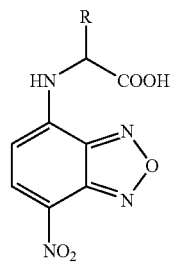
(A)

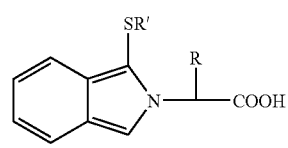
(B)

-continued (C)

R$_1$ in the aforementioned formula (I) is a hydrogen atom, or may sometimes be the ring forming carbon atom in case of the compound (B) described above. In case that the compound with amino group is an amino acid, R$_2$ means an alkyl group having at least carboxyl group as a substituent. In case that the amino acid is proline, R$_1$ and R$_2$ together form a ring. The compound with amino group includes various compounds other than amino acids. In that case, R$_2$ is an alkyl group with a substituent except carboxyl group, for example hydroxyl group, sulfonate group, and phenyl group.

In a preferable mode for carrying out the invention, the derivative of the compound with amino group is a compound represented by the following formula (II).

(II)

In formula (II), Ar$_2$ denotes a carbocyclic compound residue or a heterocyclic compound residue having an aromaticity; X denotes an oxygen atom or a sulfur atom; Y denotes an oxygen atom, a sulfur atom, a secondary amine, a tertiary amine, or an optionally substituted methylene group; R$_1$ denotes a hydrogen atom, an optionally substituted alkyl group, or a ring forming carbon atom; R$_2$ denotes an optionally substituted alkyl group; R$_1$ and R$_2$ together may form a ring.

In one mode for carrying out the invention, the derivative of a compound with amino group is a compound with phenylcarbamylamino group, a compound with 3-pyridylcarbamylamino group, a compound with phenylthiocarbamylamino group, a compound with 3-pyridylthiocarbamylamino group, a compound with p-trimethylammoniumanilylcarbamylamino group, or a compound with p-dimethylammoniumanilylcarbamylamino group.

As a reagent for derivatization so as to generate such derivative of a compound with amino group, various reagents may be used. Preferably, the reagents include for example substituted isothiocyanate aromatic compounds, substituted isocyanate aromatic compounds, substituted succinimidylcarbamate aromatic compounds, substituted carbamoylhalide aromatic compounds or substituted carbamoylalkoxy aromatic compounds represented by the following formulae III or IV.

$$Ar_2 \overset{Y}{\underset{X}{\diagdown}} \overset{R'}{\diagup} \quad (III)$$

$$Ar_2 \overset{}{\underset{}{\diagdown}} N=C=X \quad (IV)$$

In formulae (III) and (IV), $Ar_2$ denotes a carbocyclic compound residue or heterocyclic compound residue having an aromaticity; R' denotes a fluorine atom, a chlorine atom, a bromine atom, an iodine atom, an N-hydroxysuccinimidyl group or an alkoxy group; X denotes an oxygen atom or a sulfur atom; Y denotes an oxygen atom, a sulfur atom, a secondary amine, a tertiary amine or an optionally substituted methylene group.

More specifically, known compounds with high reactivity with amino group, such as those shown below in Table 2 can be used.

TABLE 2

| Name of compound | Structural formula |
|---|---|
| Phenylisocyanate | NCO-phenyl |
| Phenylisothiocyanate | NCS-phenyl |
| 3-Pyridylisocyanate | NCO-pyridyl |
| 3-Pyridylisothiocyanate | NCS-pyridyl |
| Phenyl-N-hydroxysuccinimidylcarbamate | 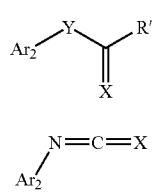 |

TABLE 2-continued

| Name of compound | Structural formula |
|---|---|
| Phenyl-N-hydroxysuccinimidyl-thiocarbamate | |
| 3-Aminopyridyl-N-hydroxysuccinimidylcarbamate | |
| 3-Aminopyridyl-N-hydroxysuccinimidylthiocarbamate | |

Otherwise, reagents for derivatization containing carbamate compounds represented by the following formula (V) as reported above in Pamphlet of International Publication WO 03/069328 by the inventors are listed in particularly preferable modes for carrying out the invention.

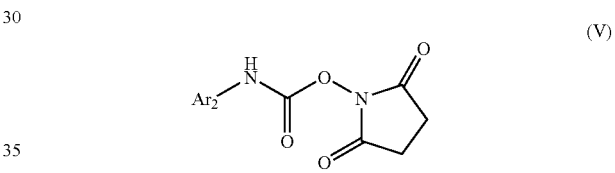

(V)

In formula (V), $Ar_2$ binding to the nitrogen atom in the carbamate group denotes a carbocyclic compound residue or heterocyclic compound residue having an aromaticity, where the aromatic ring may or may not have one or more substituents; the binding of $Ar_2$ group to the nitrogen atom in the carbamate group may satisfactorily be the binding of the carbon atom composing the ring in the $Ar_2$ group to the nitrogen atom in the carbamate group, where the carbamate compound may be in a salt form.

Concerning $Ar_2$ in formula (V), the carbocyclic compound residue includes, for example, phenyl group, naphthyl group (1- and 2-naphthyl group) and anthryl group (1-, 2- and 5-anthryl group), which individually may or may not have a substituent; the heterocyclic compound residue includes, for example, pyridyl group (2-, 3- and 4-pyridyl group), pyrazyl group, quinolyl group (2 to 8-quinolyl group), acridyl group (1 to 4- and 9-acridyl group), and coumaryl group (5 to 8-coumaryl group), which individually may or may not have a substituent. The group may have one or more substituents in the aromatic ring. The substituents include, for example, alkyl groups with one to 5 carbon atoms, aromatic groups such as naphthyl group and phenyl group, halogen atoms such as chlorine atom, bromine atom, fluorine atom and iodine atom, carboxyl group, hydroxyl group, nitro group, diazo group, cyano group, alkoxy group with one to 5 carbon atoms, acyl groups with 2 to 7 carbon atoms (acetyl group, benzoyl group and the like), sulfonate group, phosphate group, guanidyl group, dialkylamino group, and trialkylammonium group. So as to detect compounds with amino group at high sensitivity, specifically, the compounds with amino group preferably have polar substituents, particularly substituents readily ionizable in solution. The substituents include, for example, sulfonate group, phosphate group, guanidyl group, dialkylamino group and trialkylammonium group.

Specific examples of $Ar_2$ include the following groups:

Phenyl group, naphthyl group (1- and 2-naphthyl group), anthryl group (1-, 2- and 5-anthryl group), pyridyl group (2-, 3- and 4-pyridyl group), pyrazyl group, quinolyl group (3-, 6- and 8-quinolyl group), 9-acrydyl group, 6-coumaryl group, p-dialkylaminophenyl group, p-trialkylammoniumphenyl group, 1-(3-trialkylammonium)naphthyl group, 1-(5-triallylammonium)naphthyl group, 1-(3-dialkylamino)naphthyl group, 1-(5-dialkylamino)naphthyl group, p-sulfophenyl group, 1-(3-sulfo)naphthyl group, 1-(5-sulfo)naphthyl group, p-phosphophenyl group, 1-(3-phospho)naphthyl group, 1-(5-phospho)naphthyl group, p-guanidinophenyl group, 1-(3-guanidino)naphthyl group, and 1-(5-guanidino)naphthyl group. The alkyl groups in the dialkylamino group and the trialkylammonium group independently represent an alkyl group with one to 5 carbon atoms. The method for preparing these reagents for derivatization and the method for preparing amino acids using them are described in detail in Pamphlet of International Publication WO 03/069328, which is incorporated by reference in this specification.

Analytical Method of the Present Invention

It is not particularly difficult to react the compound with amino group with a reagent for derivatization (labeling reaction) by the analytical method in accordance with the invention. As the reaction conditions, general conditions in case of labeling using such reagent (see Iwaki, K., Yoshida, S., Nimura, N., Kinoshita, T., Takeda, K., and Ogura, H., Chromatographia 23 899 (1987)) may be used. Preferably, conditions for mixing a solution of a compound with amino group dissolved in an appropriate organic solvent except alcohols, in environment at about pH 8 to 10 with a reagent for derivatization, and subsequently heating the mixture to about 60° C. are preferably selected. The amount of the reagent to be used for derivatization is ranges from 10- to 1,000-fold in mole (equivalent), preferably about 100- to 1,000-fold (equivalent) in mole, that of the compound with amino group, in view of the amount of the compound with amino group, particularly the amount of total primary amines and secondary amines contained therein, so as to label all the amino groups and imino groups.

A compound with amino group, amino acid for example, can be converted to a derivative of the compound with amino group, via the reaction shown in FIG. 1. According to the reaction scheme of FIG. 1(a), it is shown that an identical derivative of the compound with amino group can be generated even if the amino acid is reacted with a different reagent for derivatization, namely phenyl-N-hydroxysuccinimidylcarbomate (PAHS) or phenylisocyanate (PIC). Similarly, FIG. 1(b) shows that the reaction of amino acid with 3-aminopyridyl-N-hydroxysuccinimidylcarbamate (APDS) or pyridylisocyanate (PyIC) can also generate an identical derivative of the compound with amino group. According to the method of the invention, therefore, the structure of the derivative of a compound with amino group as generated consequently from the reaction for derivatization is characteristically the structure represented by the formula (I) or (II). As long as the resulting structure has such structure, the method for such reaction using any reagent for derivatization is included within the scope of the invention.

The term "liquid chromatography" in the analytical method in accordance with the invention is a separation means by chromatography using liquid as a mobile phase. By selecting a column for a solid phase, liquid chromatography can be used as high performance liquid chromatography (HPLC) operable under pressure in various applications. The separation mechanism is classified into various mechanisms such as partition, adsorption, ion exchange and size exclusion. The column most frequently used is a reverse-phase solid phase, where separation is done by partition, to retain a sample on a solid phase with a lower polarity and to elute then the sample on a mobile phase with an appropriate polarity.

Figure 2:
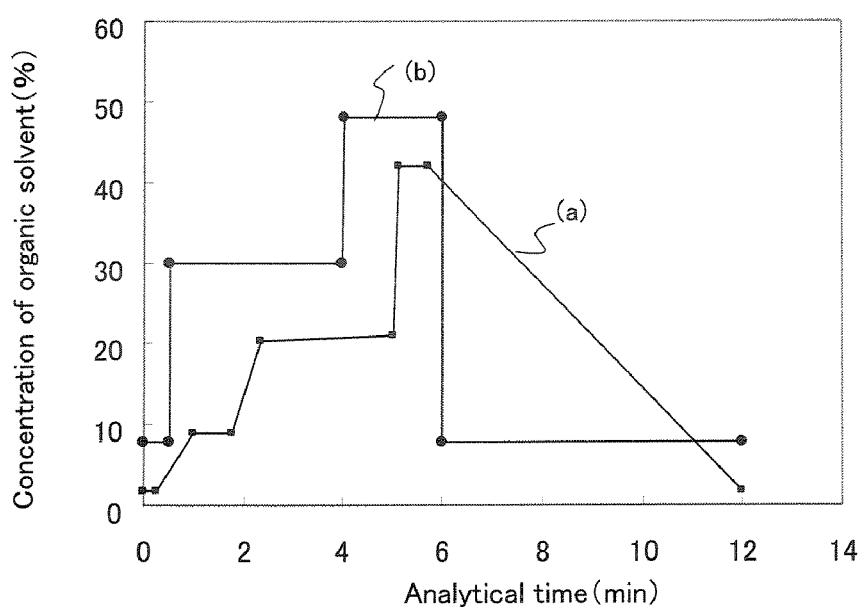
FIG. 2 shows a typical example of the stepwise elution pattern on a concentration gradient by liquid chromatography, according to the method of the invention.

The term "stepwise elution means on concentration gradient (stepwise gradient)" refers to the change of the polarity or salt intensity of the mobile phase in a stepwise manner. For example, the ratio of organic solvents contained in the eluent is modified as shown in FIG. 2. In FIG. 2, the ratio of organic solvents contained in the eluent changes in a stepwise manner as the analytical time passes, involving a non-linear change from the state without concentration gradient or with a mild concentration gradient to the state of a sharper concentration gradient. Preferably, the ratio of organic solvents is modified at least twice, more preferably three times or more, to enable efficient separation.

Herein, the optimal stepwise gradient varies, depending on the type of a derivative of a compound with amino group as an analytes and the kinds of organic solvents to be used. Additionally, because the separation capacity is improved as the elution time is longer, the same effect as in the invention may sometimes be obtained by prolonging the elution time even when an elution means on a linear concentration gradient (linear gradient method) is used.

As the organic solvents to be used, various solvents may appropriately be selected, depending on the packing agent in the column and the column size; in case of HPLC using a reverse-phase column, for example, formic acid, acetic acid, trifluoroacetic acid, propionic acid, butyric acid, pentafluoropropionic acid, and heptafluorobutyric acid are used as acids; ammonia, trimethylamine, triethylamine and tributylamine are used as bases. Additionally, solutions pH-adjusted by solutions of these salts, preferably solutions adjusted to pH 2.5 to 7.5, using aqueous 5- to 50 mM solutions of formic acid, acetic acid, ammonium formate, and ammonium acetate, are preferably used while acetonitrile, methanol, ethanol as organic solvents, and mix solutions thereof with water are preferably used.

In a preferable mode for carrying out the elution step by liquid chromatography, the difference in elution time between a derivative of a compound with amino group having the shortest elution time among histidine derivatives, aspartic acid derivatives, arginine derivatives, hydroxyproline derivatives, glutamic acid derivatives, argininosuccinic acid derivatives, cysteine sulfinic acid derivatives, cysteic acid derivatives, and β-hydroxyaspartic acid derivatives, and a derivative of a compound with amino group having the longest elution time among tryptophan derivatives, lysine derivatives, phenylalanine derivatives, 1,5-diaminopentane derivatives, homoleucine derivatives, tryptamine derivatives, homolanthionine derivatives, tyramine derivatives, cysteamine derivatives, putrescine derivatives, cysteamine derivatives and 2-phenylethylamine derivatives, can be set between 3 to 20 minutes, preferably between 3 to 10 minutes. So as to carry out the analysis rapidly, the difference in elution time is preferably set as short as possible. Taking account of the performance of a separation column to be used and the kinds or number of analytes in a sample, the difference in elution time can appropriately be set.

The mass spectrometry to be used in accordance with the invention is a method comprising ionizing the compound with amino group after elution by liquid chromatography into positive ions or negative ions by methods such as electrospray ionization method (ESI), atmospheric pressure chemical ionization method (APCI) and sonic spray ionization method (SSI) and then measuring the resulting ions in gas phase. The generated ions are subjected to a mass separation apparatus of, for example, quadrupole type, ion trap type, time of flight type and magnetic field type, to separate the ions based on the ratio of mass and electric charge. By connecting plural mass separation apparatuses like an apparatus of triple quadrupoles (MS/MS), highly selective measurement can be done.

With an apparatus of triple quadrupoles, for example, the mass of a derivative of a compound with amino group is measured with a first quadrupole; only an attention-focused derivative of a compound with amino group is transferred to a second quadrupole, where the derivative is fragmented by collision-induced dissociation (CID); then, the mass of the resulting fragment can be measured with a third quadrupole at extremely high sensitivity.

By using this and by the following two kinds of measurement methods, namely precursor ion scan method and selected reaction monitoring (SRM) method, an ion of a reaction product between a compound with amino group and the labeling reagent is detected by a first mass analyzer, while a fragment ion derived from the reagent is detected by a second mass analyzer, thus enabling highly sensitive analysis at high selectivity.

The reagent for derivatization for use in such methods includes, for example, p-dimethylaminoanilyl-N-hydroxysuccinimidylcarbamate (DAHS), 3-aminopyridyl-N-hydroxysuccinimidylcarbamate (APDS), p-trimethylammoniumanilyl-N-hydroxysuccinimidylcarbamate iodide (TAHS), aminopyrazyl-N-hydroxysuccinimidylcarbamate, 6-aminoquinolyl-N-hydroxysuccinimidocarbamate (AQC), and 9-aminoacrylidyl-N-hydroxysuccinimidocarbamate.

In case that a compound with a small ionizing capacity is selected as a reagent for derivatization among the carbamate compounds, selective cleavage occurs similarly by CID. When a mass analyzer is set so as to observe cation in the mass analyzer, the reagent-derived structure receives neutral loss so that [amino acid+H] is observed as a fragment ion. By using this and by constant neutral loss scan method, a mass analyzer is set to observe cation, so that an ion as a reaction product between amino acid and a reagent can be detected by a first mass analyzer, while the amino acid-derived ion from the neutral loss of the reagent backbone-derived structure is detected by a second mass analyzer. Thus, extremely highly selective and highly sensitive amino acid analysis can be done. The reagent for derivatization for use in such method includes 1-naphthylamino-N-hydroxysuccinimidylcarbamate (NAHS).

Preferable Mass Spectrometry Method

The mass spectrometry method for use in accordance with the invention is introduced in but is not limited to some preferable examples.

Selected Ion Monitoring:

By selected ion monitoring (SIM), only a specific m/z ratio preliminarily selected is monitored for detecting a compound with the intended mass at high precision.

Precursor Ion Scan:

By precursor ion scan analysis, a defined mass range is scanned with a first mass analyzer (Q1 and the like); and ions within the range are dissociated by collision-induced dissociation on for example Q2. A second mass analyzer (Q3 and the like) then is preset to select a specific fragment ion (for example, m/z=177 in case of TAHS). Precursor ions (parent ions) generating the specific fragment ion are recorded on the resulting spectrum.

Selected Reaction Monitoring:

By selected reaction monitoring (SRM) analysis, a subject ion is selected by a first mass analyzer (Q1 and the like); the ion is dissociated in a collision cell, to select a specific fragment ion (for example, m/z=177 in case of TAHS) by a second mass analyzer (Q3 and the like) for monitoring. Even in the presence of a contaminating component with the same retention time as that of the subject compound to be assayed and with the same mass as that of the precursor ion, the influences of the contaminating component can be excluded unless the contaminating component generates the fragment ion of the subject compound to be assayed. Accordingly, the sensitivity and selectivity can be improved greatly.

Constant Neutral Loss Scan:

By constant neutral loss scan, a defined mass range is scanned with a first mass analyzer (Q1 and the like); and ions within the range are dissociated by collision-induced dissociation on for example Q2. A second mass analyzer (Q3 and the like) then is preset to select a specific neutral fragment (for example, m/z=170 in case of 1-naphthylamino-N-hydroxysuccinimidylcarbamate). For the resulting spectrum, a scan method for detecting all the precursor ions (parent ions) with specific neutral ions to be eliminated therefrom is selected.

Because ions due to the mass of an analyte can be detected by mass spectrometry, mass spectrometry has been used widely as a detection method at extremely high selectivity. In accordance with the invention, a reagent for derivatization which induces constant cleavage in an analyte is designed, to obtain a method for detecting a compound with amino group at high selectivity. In case that a reagent for preparing a derivative with high ionizing capacity is designed, additionally, highly sensitive analysis of a compound with amino group can be attained.

By mass spectrometry, generally, contaminants exist in a low-molecular region, causing noise and blocking the detection potency for analytes. However, the introduction of one or more aromatic rings into a reagent for derivatization raises the molecular weight to attain an assay in a region with less noise.

The detection limit of amino acid varies depending on the type of amino acid. In case that the SRM mode is selected while a quadrupole mass spectrometer, for example, a detector of API 365 type (Applied BioSystems) is used, the detection limit for p-trimethylammoniumanilyl-N-hydroxysuccinimidylcarbamate iodide (TAHS) is about 2 to 40 fmol; the detection limit for p-dimethylaminoanilyl-N-hydroxysuccinimidylcarbamate (DAHS) is about 3 to 2000 fmol; the detection limit for 3-aminopyridyl-N-hydroxysuccinimidylcarbamate (APDS) is about 3 to 180 fmol; and the detection limit for 6-aminoquinolyl-N-hydroxysuccinimidocarbamate (AQC) is about 2 to 200 fmol. It is verified that these detection limits are equal or superior to those with general fluorescence-labeling reagents. Particularly, it is reported that the detection limit with 6-aminoquinolyl-N-hydroxysuccinimidocarbamate (AQC) commercially available as a fluorescence-labeling reagent is several hundreds fmol. It is found that the sensitivity of the SRM measurement is equal to that of the fluorescent method or is improved by hundred times at maximum.

Because the detection by the method of the invention is via ions derived from the mass of a compound with amino group after derivatization and labeling, analytes can be assayed by the method with no blocking with compounds except the compound, for example labeling reagents, hydrolysates of labeling reagents, and additionally unexpected contaminants formed via the labeling reaction.

In accordance with the invention, the assay precision thereof can be improved by using a stable isotope-containing compound with amino group. The assay precision can be raised by a method by means of a compound with amino group, which contains stable isotopes with small naturally occurring ratios, such as $^{13}C$, $^{2}H(D)$, $^{15}N$ and $^{18}O$, or contains a radioisotope, as an internal standard, or by using a compound with amino group after derivatization with a reagent containing the isotopes as an internal standard, to reduce the influences of the matrix effect on the analysis of biological samples and also reduce the following influences over the suppression of ionization, to raise the assay precision. By selecting an optimal internal standard, depending on the type of a compound with amino group as a analytical subject, the concentration thereof in a sample and the analytical conditions, the assay precision can greatly be improved. Preferably, all internal standards for compounds with amino group as analytical subjects are used.

In a preferable mode for carrying out the invention, two or more derivatives of compounds with amino group as selected from the group (a) and two or more derivatives of compounds with amino group as selected from at least one of the groups (b) to (i) can be selected and detected individually at the detection steps of the mass spectrometry described above.

(a) ε-Amino-n-caproic acid, leucine derivatives, isoleucine derivatives, and norleucine derivatives.

(b) Sarcosine derivatives, β-alanine derivatives, and alanine derivatives.

(c) γ-Amino-n-butyric acid derivatives, β-aminoisobutyric acid derivatives, α-amino-n-butyric acid derivatives, α-aminoisobutyric acid derivatives, and β-amino-n-butyric acid derivatives.

(d) 1-Methylhistidine derivatives and 3-methylhistidine derivatives.

(e) Homoserine derivatives, and threonine derivatives.

(f) 5-Aminovaleric acid derivatives, valine derivatives and norvaline derivatives.

(g) 4-Hydroxybenzoic acid derivatives, anthranilic acid derivatives.

(h) Glutamic acid derivatives, O-acetylserine derivatives.

(i) Anserine derivatives, homocarcinone derivatives.

In each group of (a) through (i), derivatives of compounds with amino group having an identical mass are shown. According to the method of the invention, conditions for the elution step can be preset so as to separate and detect individual derivatives of compounds with amino group as included in these individual groups. Therefore, these can be analyzed simultaneously, using a sample containing many kinds of compounds with amino group. The method of the invention therefore includes a method using a sample containing at least two or more compounds with amino group as selected from leucine, isoleucine and norleucine for simultaneously analyzing these plural derivatives of compounds with amino group, although samples containing all the compounds with amino group may satisfactorily be used according to the method.

Analytical Apparatus of the Invention

Figure 3:
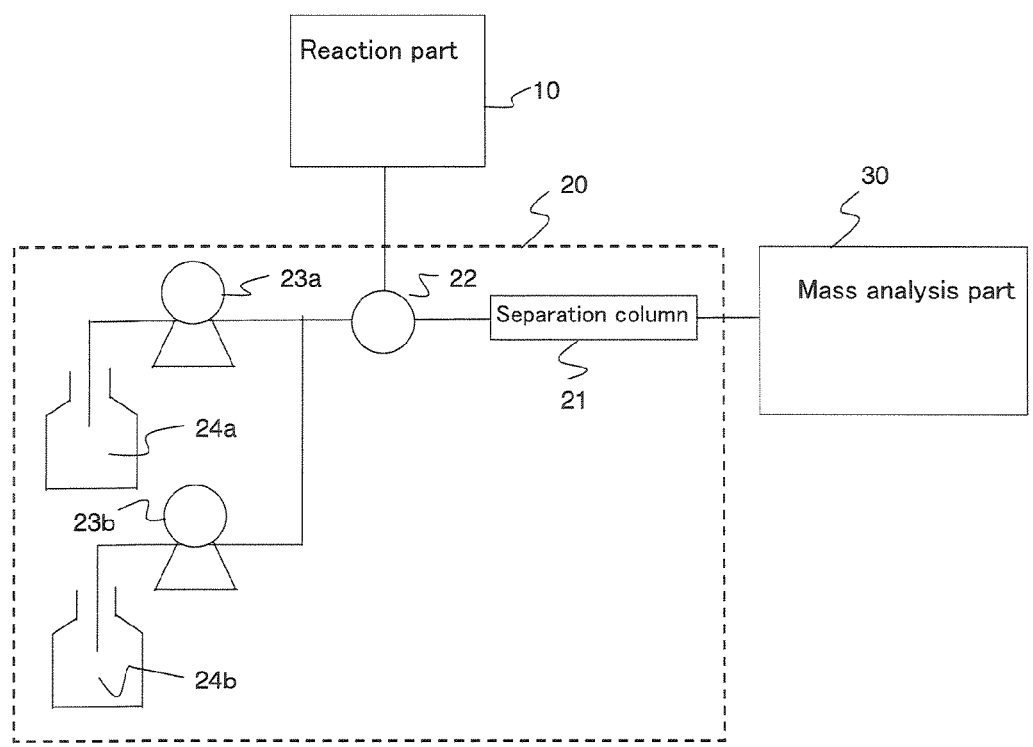
FIG. 3 shows a structural view of an apparatus for analyzing compounds with amino group, in according with one mode for carrying out the invention.

As shown in FIG. 3, for example, the analytical apparatus of the invention comprises structural elements (parts) required for carrying out the analytical method in accordance with the invention. These structural elements include at least, for example, reaction part 10 for reacting a compound with amino group in sample with a reagent for derivatization, chromatography part 20 for eluting a derivative of the compound with amino group as generated in the reaction part 10 by liquid chromatography, and mass spectrometry part 30 for detecting the derivative of the compound with amino group as contained in the eluted solution from the chromatography part 20. The elution part 20 includes separation column 21, and an elution system for supplying an elution solution with a stepwise concentration gradient into the column, for example pump 23a (23b) for feeding eluent 24a (24b) into the column. So as to prepare a concentration gradient in the elution solution, plural pumps (23a, 23b) may be used. Additionally, the chromatography part 20 is equipped with injection valve 22 for introducing the derivative of the compound with amino group as generated at the reaction part 10.

The derivative of the compound with amino group as eluted from the chromatography part 20 is first ionized with the mass spectrometry part 30. As the technique most generally used for ionizing samples such as proteins and peptides, for example, electro-spray ionization method (ESI), atmospheric pressure chemical ionization method (APCI) and matrix-assisted laser desorption ionization method (MALDI), and sonic spray ionization method (SSI) are listed. For the apparatus of the invention, the ESI method is preferably used as the method for ionizing the derivative of the compound with amino group as contained in an elution solution from liquid chromatography. Numerous systems equipped for ionization methods for efficient thermal conduction and gas preparation are used.

At the mass spectrometry part 30, continuously, ions are separated within the mass-to-electron charge ratio (m/z) selected from the ionized sample. The mass spectrometry part plays an important part in the sensitivity of analytical data and the resolution, the accurate mass and the abundance of the information obtained from mass spectrum data. The method for separating ions is classified currently into six kinds of basic kinds: magnetic field type, electric field type, ion trap type, time of flight type (TOF), quadrupole type, and Fourier transform cyclotron type. These individually have advantages and disadvantages and are used singly or in combination thereof to each other. For ESI ionization, generally, a quadrupole analytical part is used. With the newest quadrupole mass spectrometer (for example with API 4000 (Applied BioSystems)), the detection limit of amino acids after labeling with p-trimethylammoniumanilyl-N-hydroxysuccinimidylcarbamate iodide (TAHS) is 1 fmol or less for almost all of the amino acids.

The analytical apparatus of the invention can be automated from the reaction part 10 to the mass spectrometry part 30, by automatically connecting the individual structural elements (units) together. For example, a unit to conserve samples such as plasma in a 96-well plate is added, where a given amount of a sample is taken out of the unit to transfer the sample into the reaction part 10 by the automatic sampling apparatus; further, a compound with amino group can be injected automatically into the chromatography part 20, using, for example, an auto-sampler of liquid chromatography. In such manner, analysis at a very great high-throughput can be done.

By the method of the invention, 100 kinds or more of compounds with amino group including biological amino acids can be analyzed in an extremely short time, such as within 10 minutes. Thus, the method is useful in fields of foods, pharmaceutical products, medicine, and analytical apparatuses in relation with these compounds with amino acid.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if is explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Specific Procedure 1 for Derivatization of Compound with Amino Group

60 µl of a borate buffer (200 mM borate salt, 5 mM EDTA) was added to 20 µl of an amine standard solution as a sample containing compounds with amino group. 20 µl of a labeling reagent solution (5 mg of a reagent for derivatization in 1 mL of acetonitrile of HPLC grade) was added to the resulting mixture. The resulting mixture was heated at 55° C. for 10 minutes. After heating, the mixture of the derivatives of the compounds with amino group was separated by reverse-phase liquid chromatography, and then introduced in a mass spectrometry apparatus. The mixture of the resulting derivative has been previously diluted 10-fold with mobile phase A of liquid chromatography.

(1) Mobile phase A: an aqueous solution of 50 mM acetate adjusted with aqueous ammonia to pH 6.0.
(2) Mobile phase B: a solution in mixture at a ratio of 4:6 between aqueous solution of 125 mM acetate adjusted with aqueous ammonia to pH 6.0 and methanol.
(3) HPLC: Agilent HP 1100 series
(4) Detector: Mass spectrometry apparatus Sciex API 4000
(5) Temperature: 40° C.

Example 2

Analytical Example 1

A derivative mixture of 40 kinds of compounds with amino group as prepared with p-trimethylammoniumanilyl-N-hyroxysuccinimidylcarbamate iodide (TAHS) under the reaction conditions described above in the Example 1 were separated by reverse-phase HPLC, and then detected by selected ion monitoring (positive ion mode).

CAPCELL PAK AQ of a 2.0-mm inner diameter, a 50-mm length and a 3-µm particle diameter (Shiseido) was used as the separation column for reverse-phase HPLC at a flow rate of 0.3 mL/min under the following gradient conditions: time (ratio of mobile phase B) 0 to time 0.25-min (3%), time 0.25-min to time 1-min (3% to 15%), time 1-min to time 1.75-min (15%), time 1.75-min to time 2.35-min (15% to 34%), time 2.35-min to time 5-min (34% to 35%), time 5.01-min to time 5.1-min (50% to 70%), time 5.1-min to time 5.7-min (70%), and time 5.71-min to time 12-min (3%). Herein, the gradient pattern of the methanol concentration is shown in FIG. 2(a).

Figure 4A:
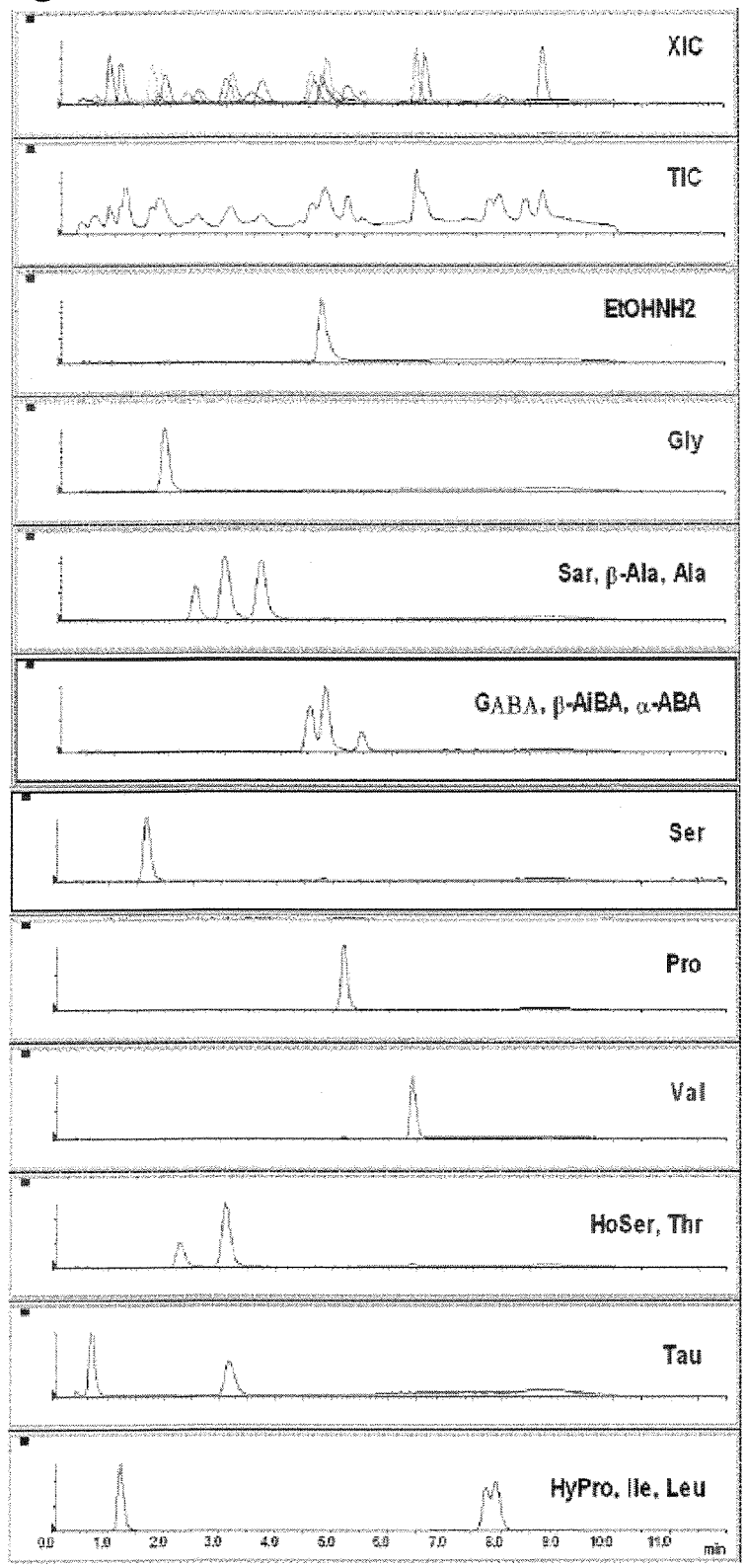
FIG. 4(a) shows a chromatogram depicting the results of the analysis of 40 kinds of compounds with amino group in Example 2: Analytical Example 1.
Figure 4B:
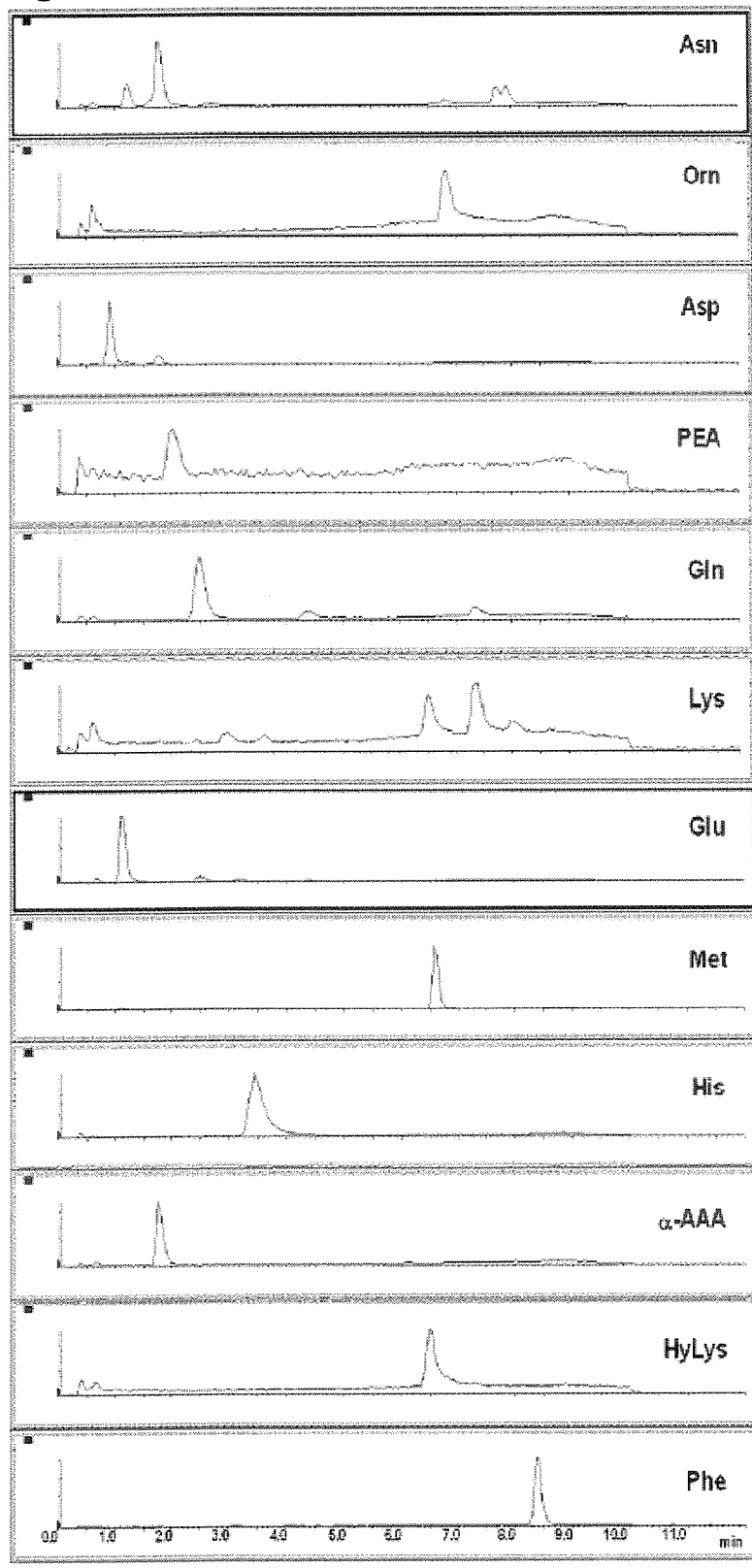
FIG. 4(b) shows a chromatogram depicting the results of the analysis of 40 kinds of compounds with amino group in Example 2: Analytical Example 1.
Figure 4C:
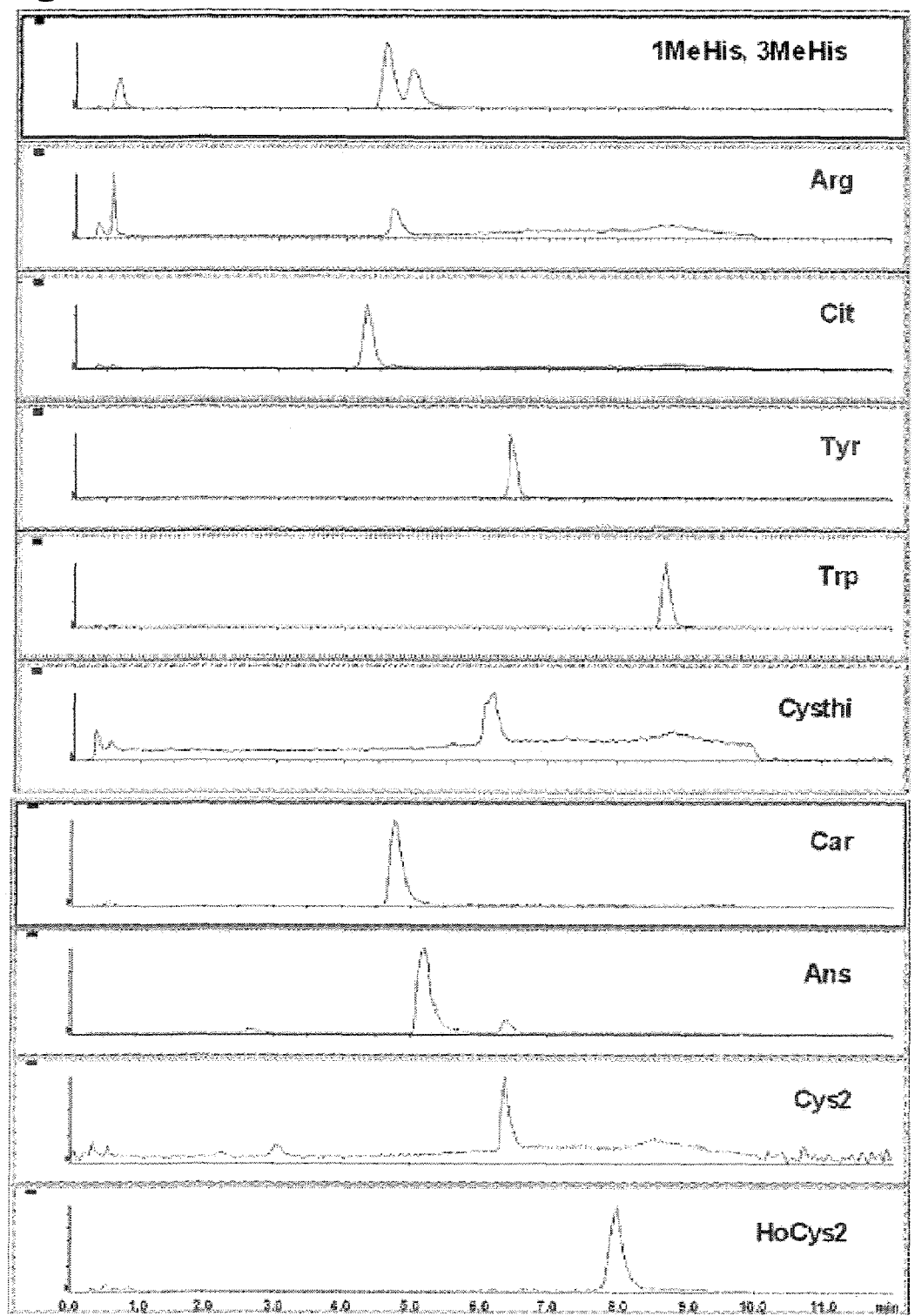
FIG. 4(c) shows a chromatogram depicting the results of the analysis of 40 kinds of compounds with amino group in Example 2: Analytical Example 1.

The analytical results are shown in FIG. 4. TIC (total ion chromatogram) continuously shows the elution patterns of 40 kinds of the compounds with amino group. Extracted ion chromatogram (XIC) shows patterns of these separated and detected 40 kinds of the compounds. Additionally, those compounds with amino group are detected singly or in mixtures of several of the kinds, and their patterns are shown below the aforementioned patterns. As apparently shown in FIG. 4, the individual 40 kinds of the compounds with amino group can be separated and detected in about 9 minutes.

Example 3

Analytical Example 2

A derivative mixture of 40 kinds of compounds with amino group as prepared with p-trimethylammoniumanilyl-N-hyroxysuccinimidylcarbamate iodide (TAHS) under the reaction conditions described above in the Example 1 were separated by reverse-phase HPLC, and then detected by selected reaction monitoring (positive ion mode).

CAPCELL PAK AQ of a 2.0-mm inner diameter, a 50-mm length and a 3-µm particle diameter (Shiseido) was used as the separation column for reverse-phase HPLC at a flow rate of 0.3 mL/min under the following gradient conditions: time (ratio of mobile phase B) 0 to time 0.25-min (3%), time 0.25-min to time 1-min (3% to 15%), time 1-min to time 1.75-min (15%), time 1.75-min to time 2.35-min (15% to 34%), time 2.35-min to time 5-min (34% to 35%), time 5.01-min to time 5.1-min (50% to 70%), time 5.1-min to time 5.7-min (70%), and time 5.71-min to time 12-min (3%).

Figure 5A:
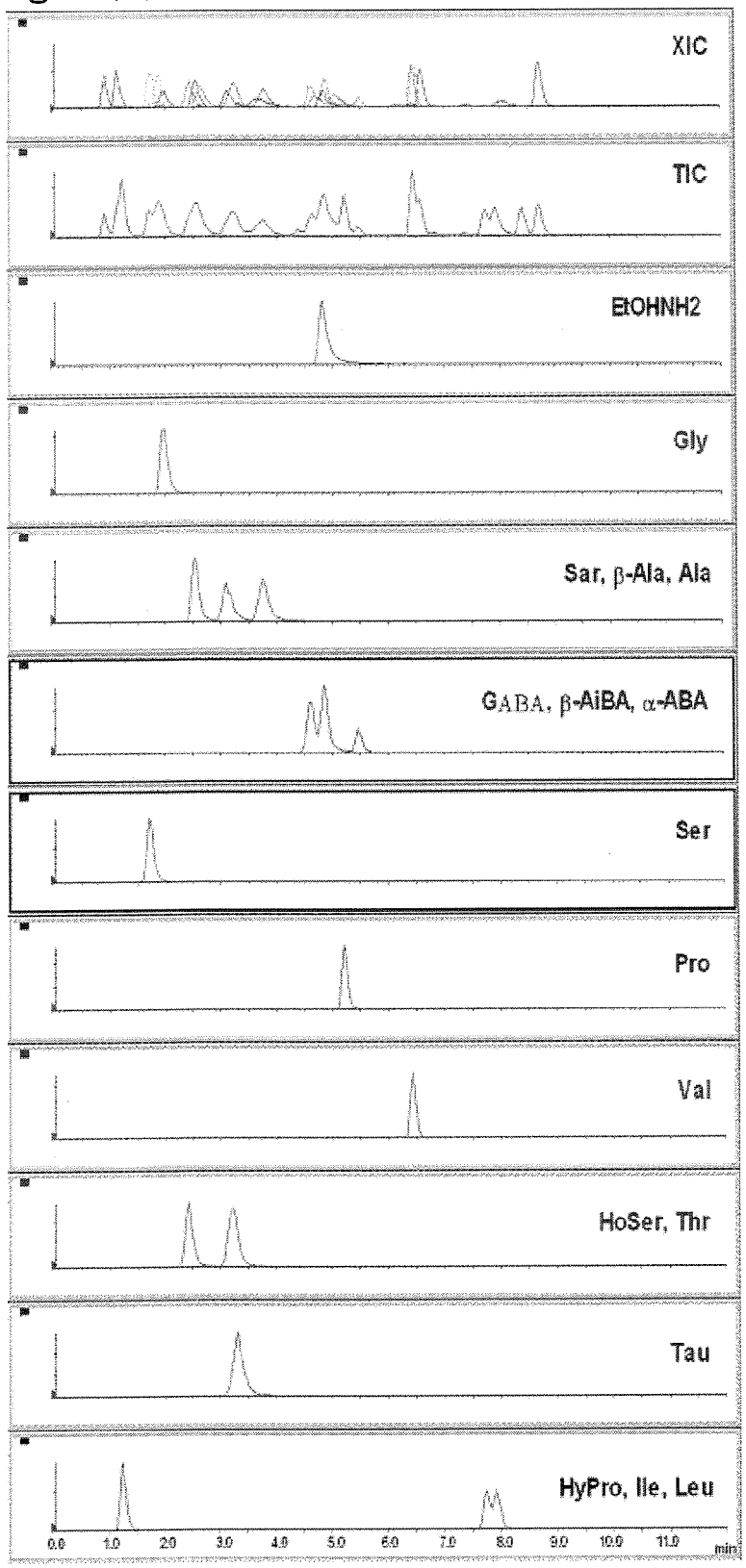
FIG. 5(a) shows a chromatogram depicting the results of the analysis of 40 kinds of compounds with amino group in Example 3: Analytical Example 2.
Figure 5B:
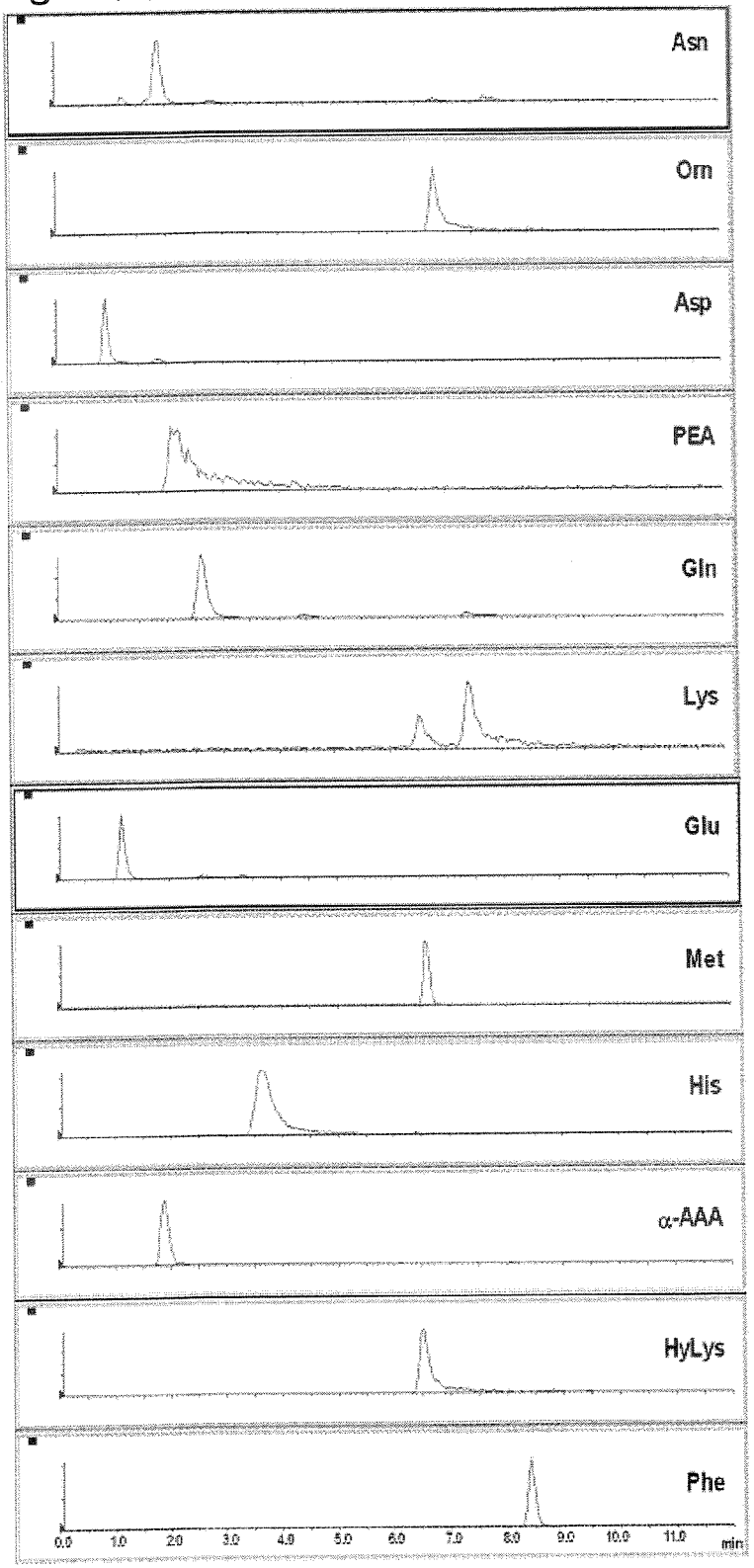
FIG. 5(b) shows a chromatogram depicting the results of the analysis of 40 kinds of compounds with amino group in Example 3: Analytical Example 2.
Figure 5C:
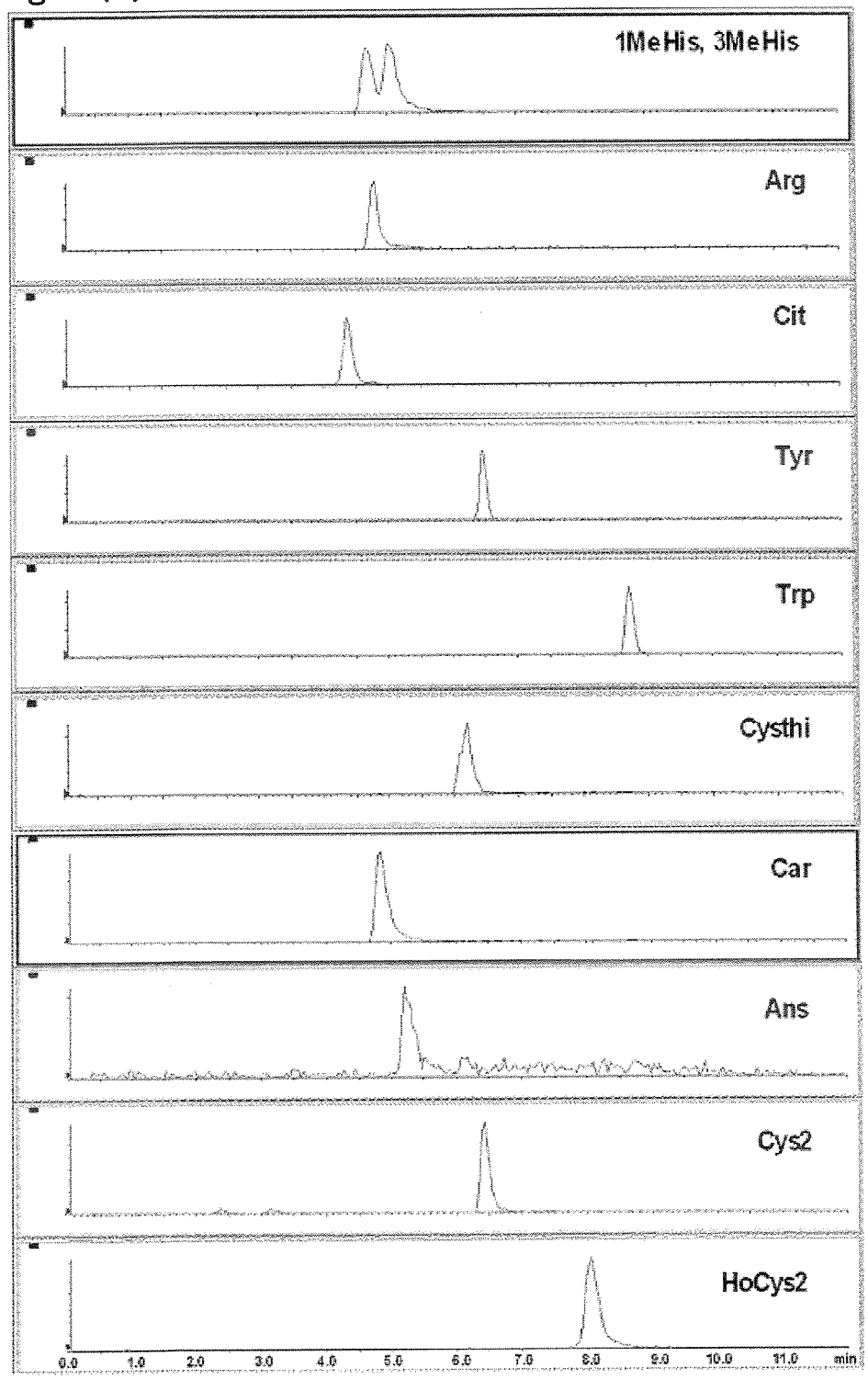
FIG. 5(c) shows a chromatogram depicting the results of the analysis of 40 kinds of compounds with amino group in Example 3: Analytical Example 2.

The analytical results are shown in FIG. 5. As in the above Analytical Example 1, the individual 40 kinds of the compounds with amino group were separated and detected in about 9 minutes in this Analytical Example.

Example 4

Analytical Example 3

A derivative mixture of 39 kinds of compounds with amino group as prepared with 3-aminopyridyl-N-hyroxysuccinimidylcarbamate (APDS) under the reaction conditions described above in the Example 1 were separated by reverse-phase HPLC, and then detected by selected ion monitoring (positive ion mode).

CAPCELL PAK AQ of a 2.0-mm inner diameter, a 50-mm length and a 3-µm particle diameter (Shiseido) was used as the separation column for reverse-phase HPLC at a flow rate of 0.3 mL/min under the following gradient conditions: time (ratio of mobile phase B) 0 to time 0.5-min (13%), time 0.51-min to time 4-min (50%), time 4.01-min to time 6-min (80%), and time 6.01-min to time 12-min (13%). Herein, the gradient pattern of the methanol concentration is shown in FIG. 2(b).

Figure 6A:
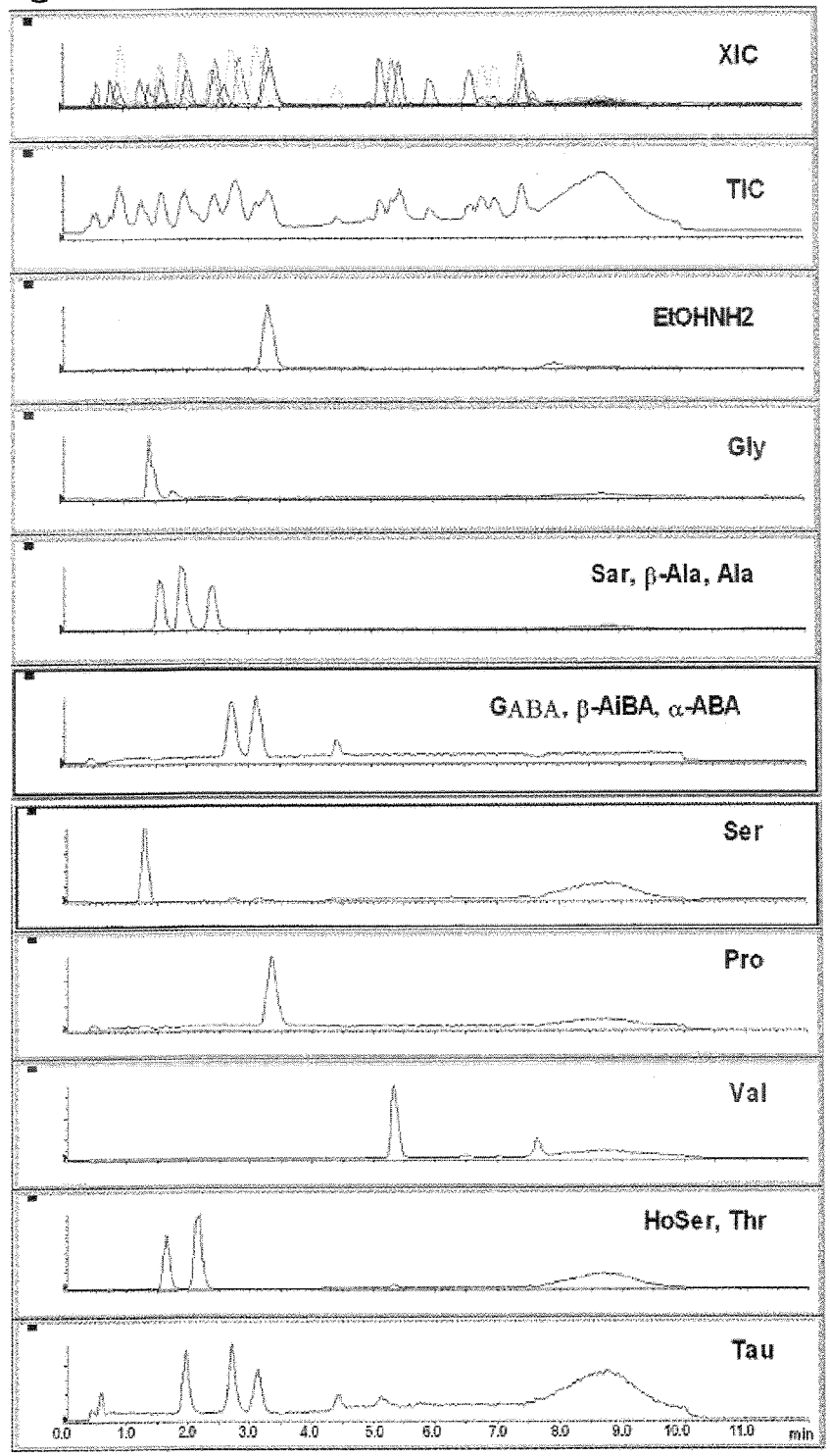
FIG. 6(a) shows a chromatogram depicting the results of the analysis of 39 kinds of compounds with amino group in Example 4: Analytical Example 3.
Figure 6B:
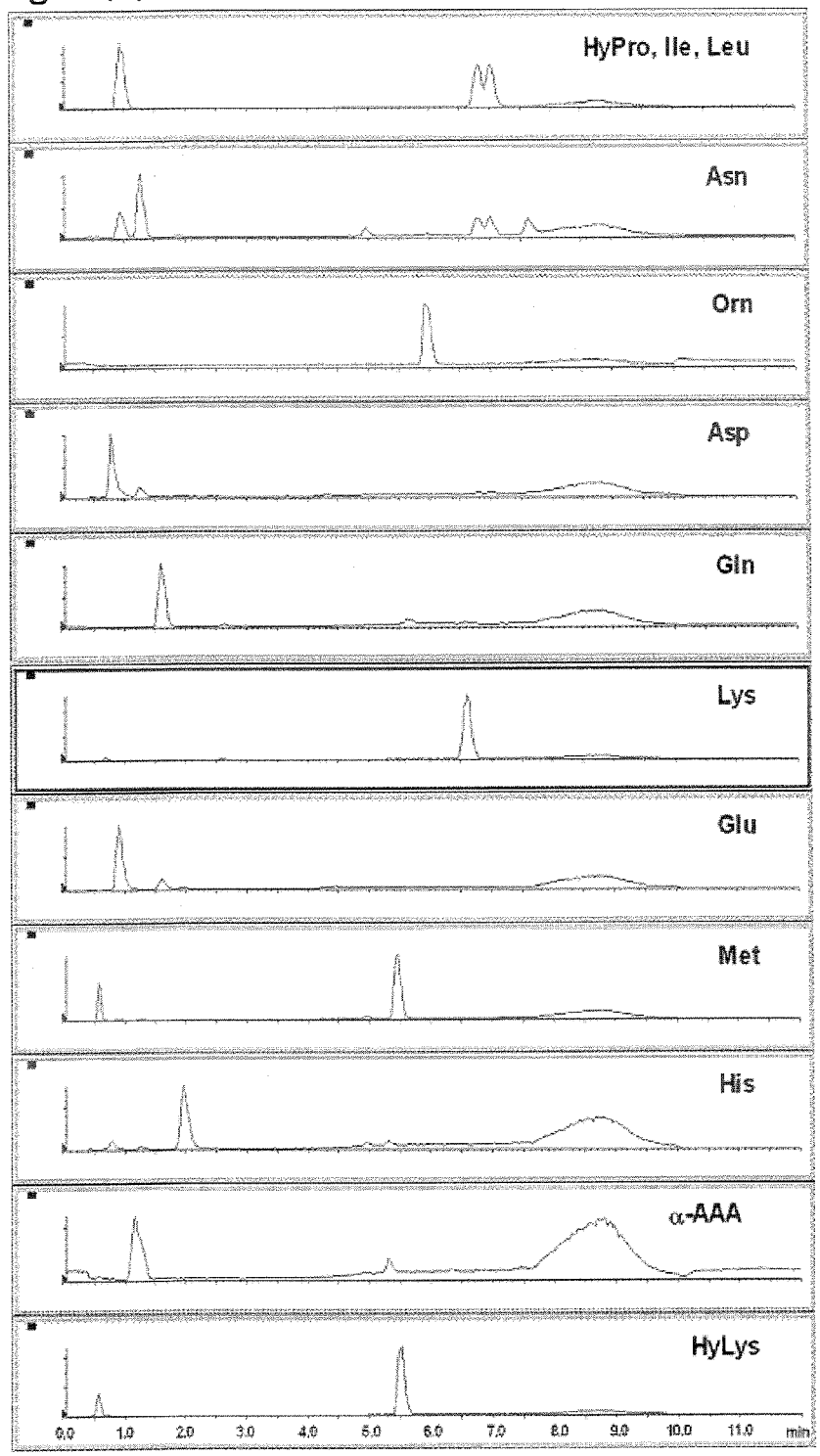
FIG. 6(b) shows a chromatogram depicting the results of the analysis of 39 kinds of compounds with amino group in Example 4: Analytical Example 3.
Figure 6C:
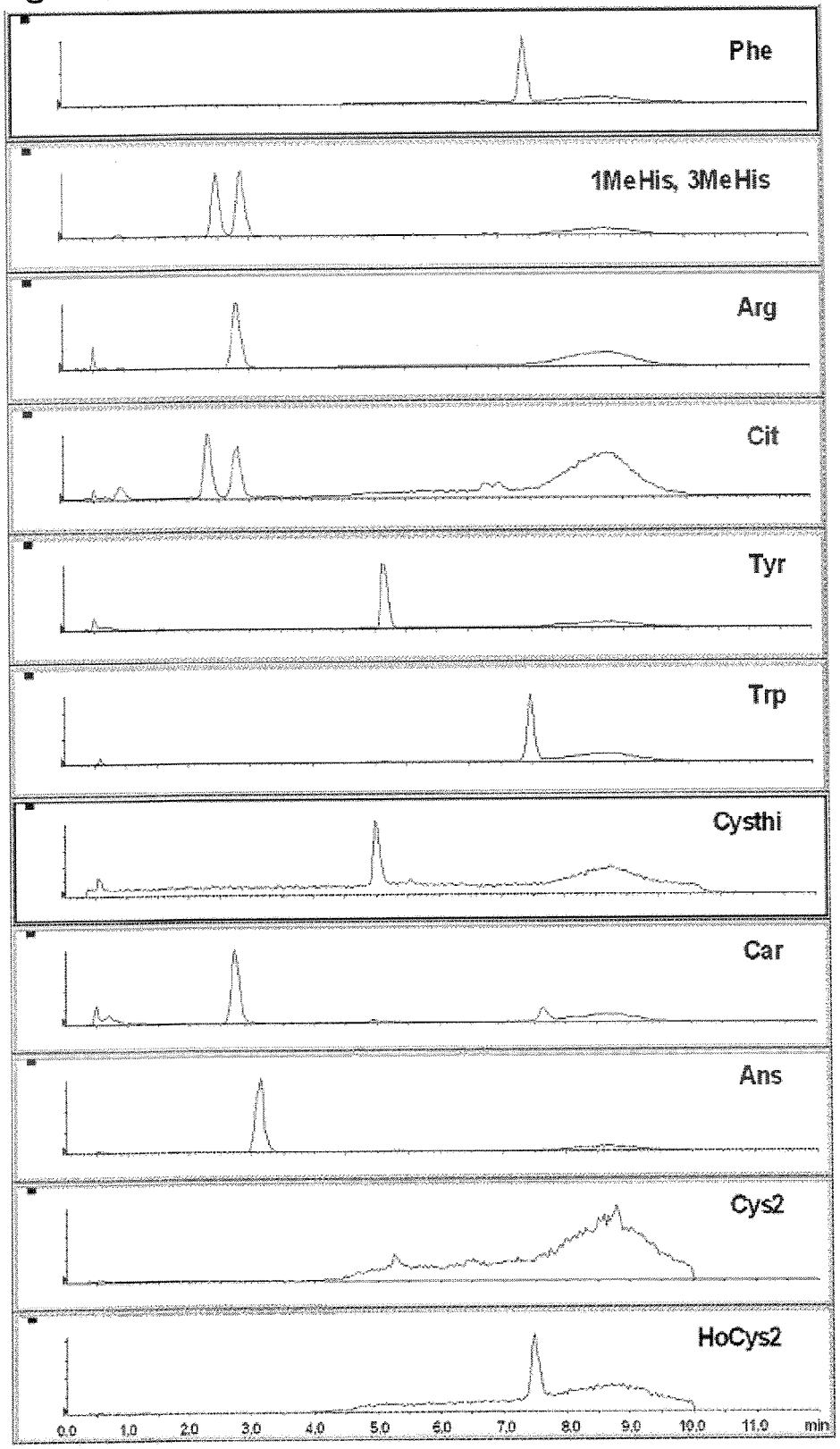
FIG. 6(c) shows a chromatogram depicting the results of the analysis of 39 kinds of compounds with amino group in Example 4: Analytical Example 3.

The analytical results are shown in FIG. 6. As in the above Analytical Examples 1 and 2, the individual 39 kinds of the compounds with amino group can be separated and detected in about 8 minutes in this Analytical Example.

Example 5

Analytical Example 4

A derivative mixture of 39 kinds of compounds with amino group as prepared with 3-aminopyridyl-N-hyroxysuccinimidylcarbamate (APDS) under the reaction conditions described above in the Example 1 were separated by reverse-phase HPLC, and then detected by selected reaction monitoring (positive ion mode).

CAPCELL PAK AQ of a 2.0-mm inner diameter, a 50-mm length and a 3-μm particle diameter (Shiseido) was used as the separation column for reverse-phase HPLC at a flow rate of 0.3 mL/min under the following gradient conditions: time (ratio of mobile phase B) 0 to time 0.5-min (13%), time 0.51-min to time 4-min (50%), time 4.01-min to time 6-min (80%), and time 6.01-min to time 12-min (13%).

Figure 7A:
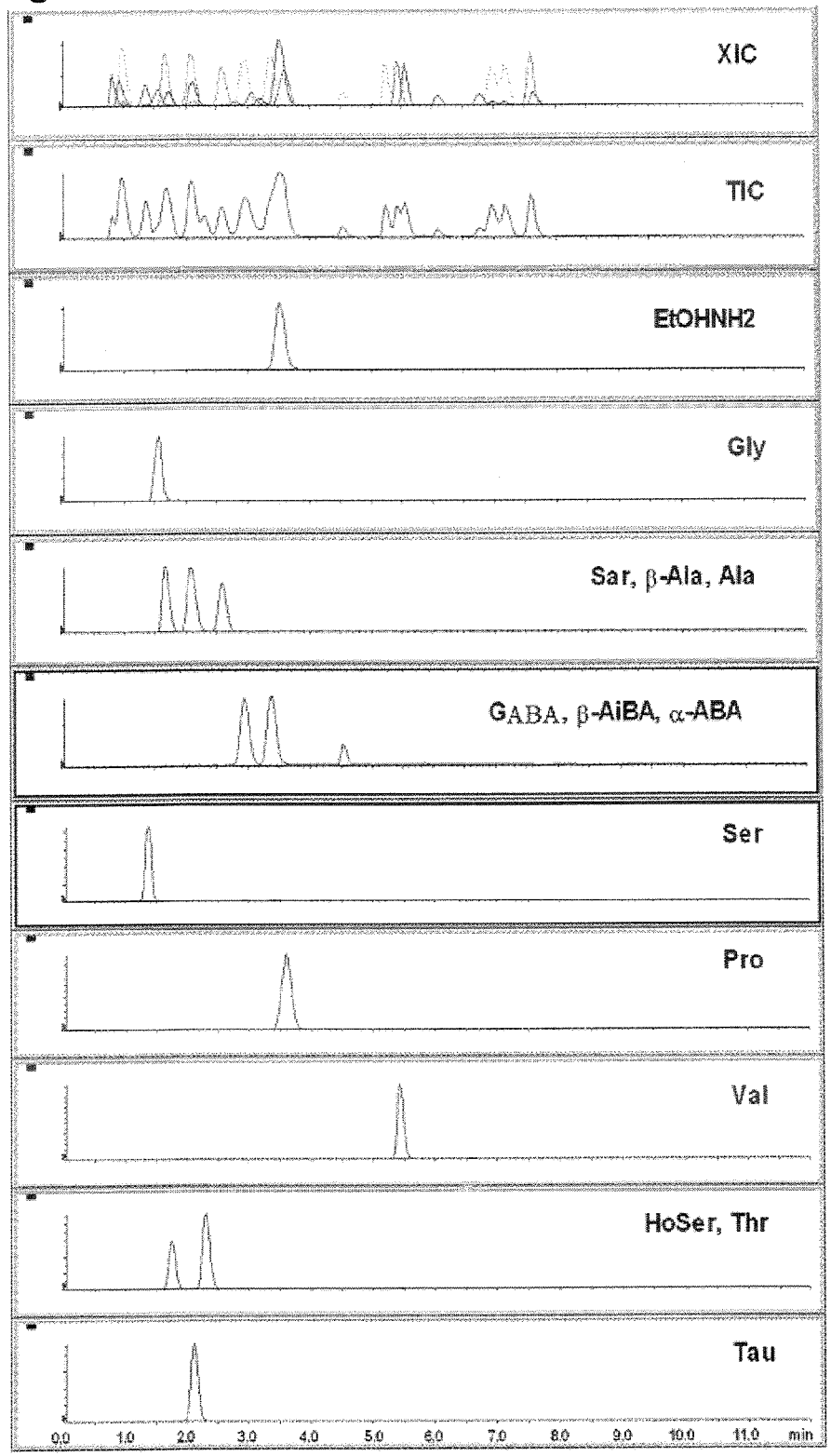
FIG. 7(a) shows a chromatogram depicting the results of the analysis of 39 kinds of compounds with amino group in Example 5: Analytical Example 4.
Figure 7B:
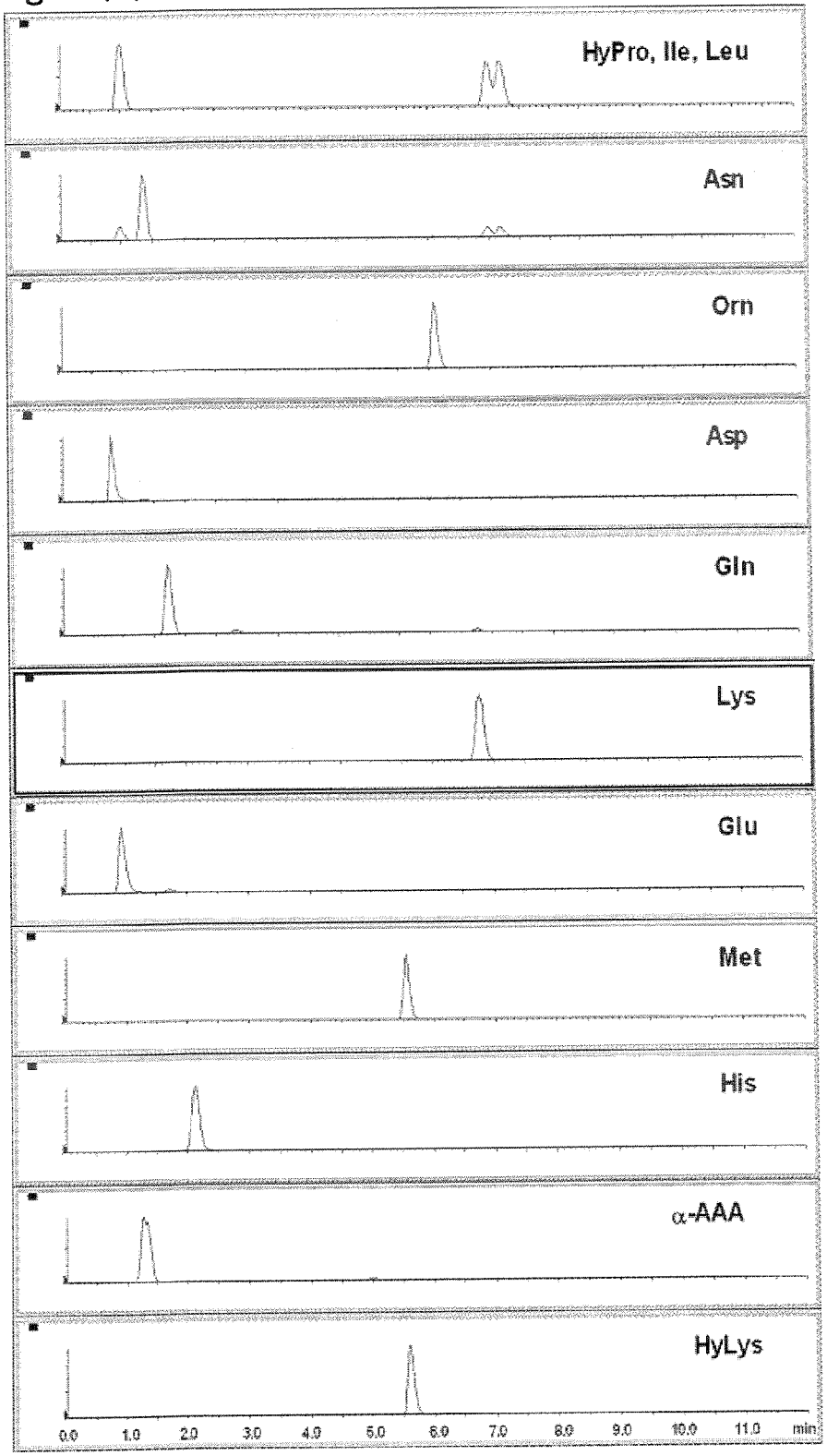
FIG. 7(b) shows a chromatogram depicting the results of the analysis of 39 kinds of compounds with amino group in Example 5: Analytical Example 4.
Figure 7C:
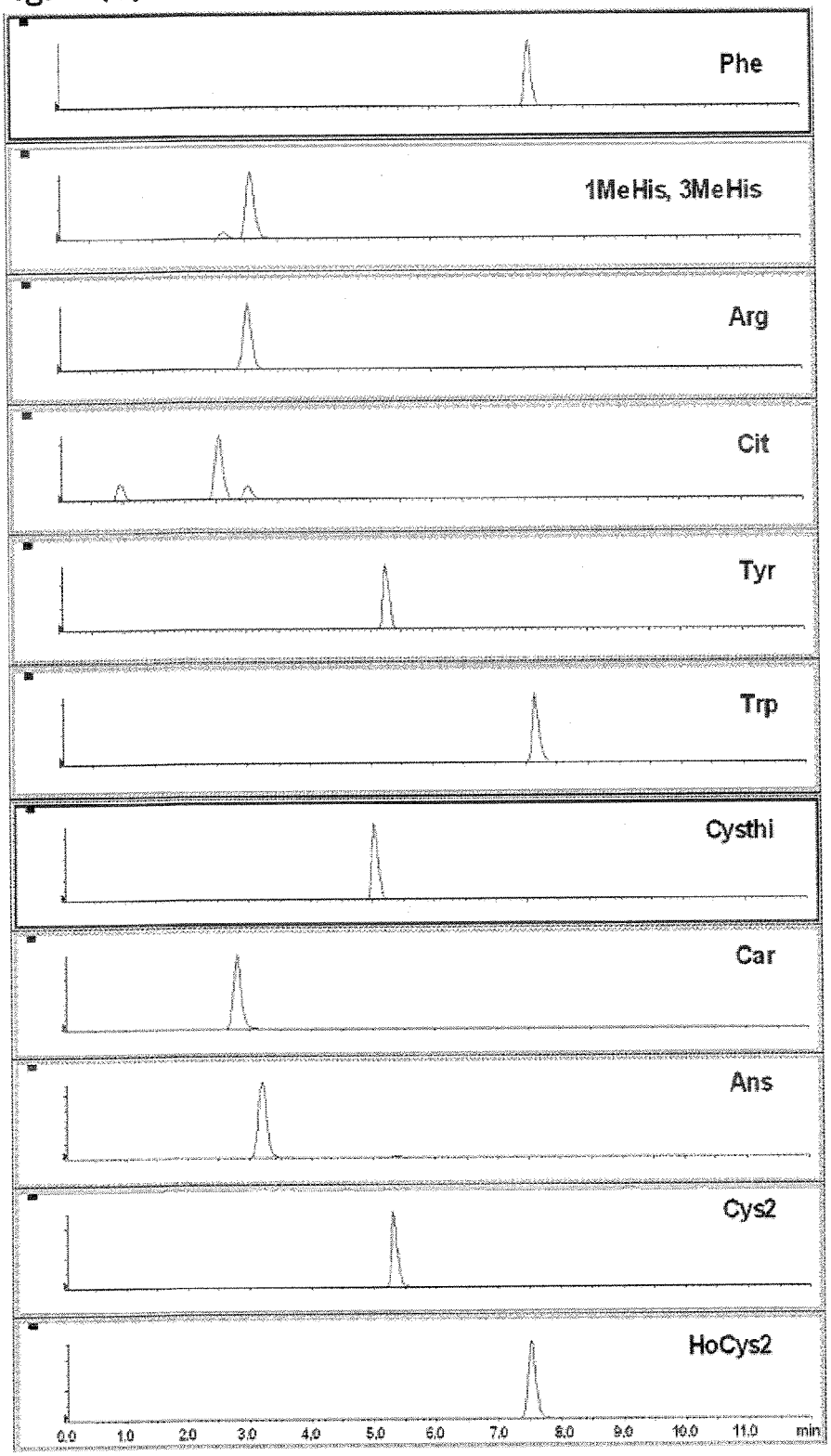
FIG. 7(c) shows a chromatogram depicting the results of the analysis of 39 kinds of compounds with amino group in Example 5: Analytical Example 4.

The analytical results are shown in FIG. 7. As in the above Analytical Examples 1 to 3, the individual 39 kinds of the compounds with amino group were separated and detected in about 8 minutes in this Analytical Example.

Example 6

Analytical Example 5

A derivative mixture of 39 kinds of compounds with amino group as prepared with phenylisocyanate (PIC) under the reaction conditions described above in the Example 1 were separated by reverse-phase HPLC, and then detected by selected ion monitoring (positive ion mode).

SuperODS of a 2.0-mm inner diameter, a 50-mm length and a 2-μm particle diameter (TOSOH) was used as the separation column for reverse-phase HPLC at a flow rate of 0.4 mL/min under the following gradient conditions: time (ratio of mobile phase B) 0 to time 0.01-min (13%), time 0.01-min to time 2-min (60%), time 2.5-min to time 4.5-min (100%), and time 4.51-min to time 10-min (13%).

Figure 8A:
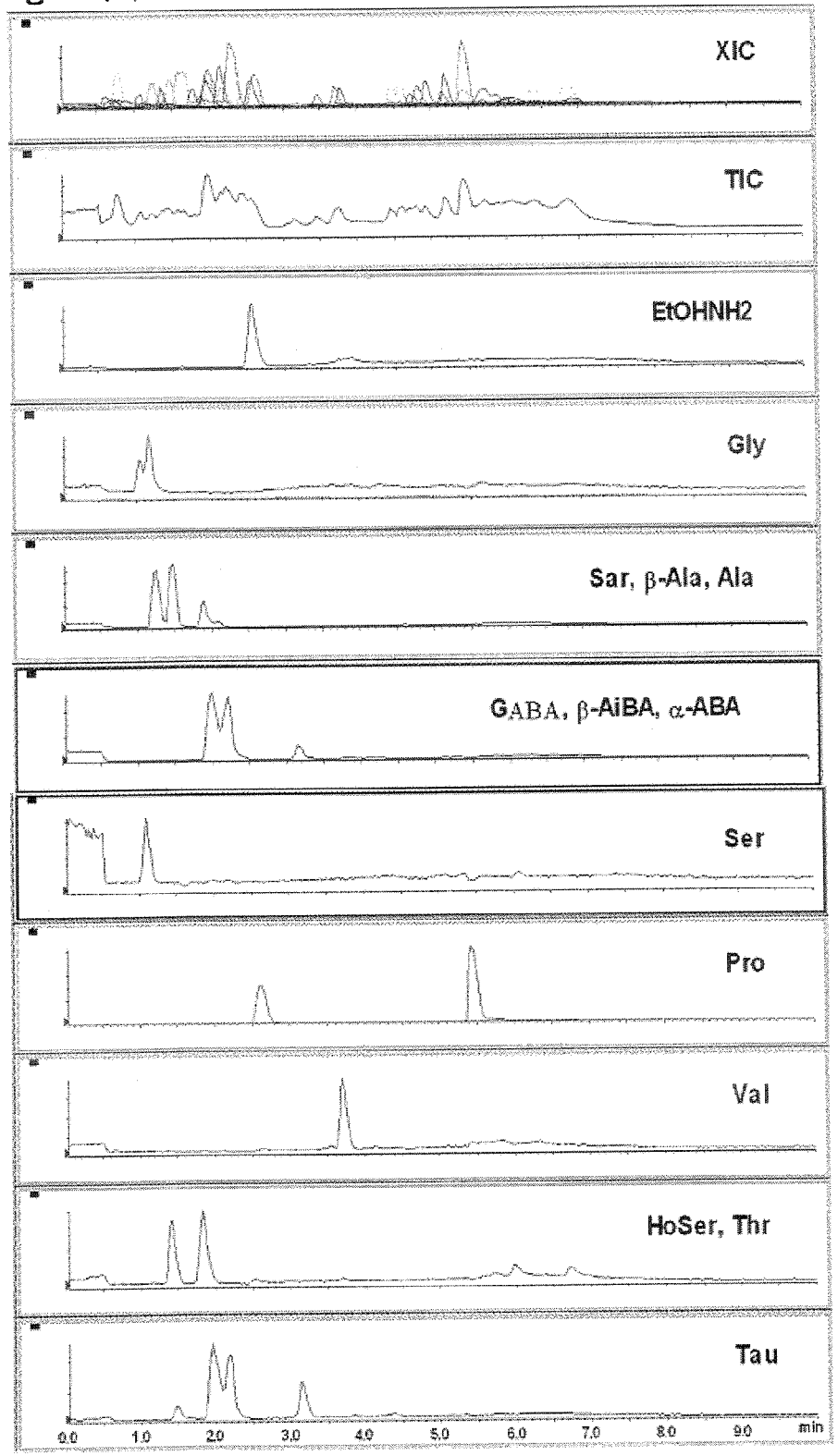
FIG. 8(a) shows a chromatogram depicting the results of the analysis of 39 kinds of compounds with amino group in Example 6: Analytical Example 5.
Figure 8B:
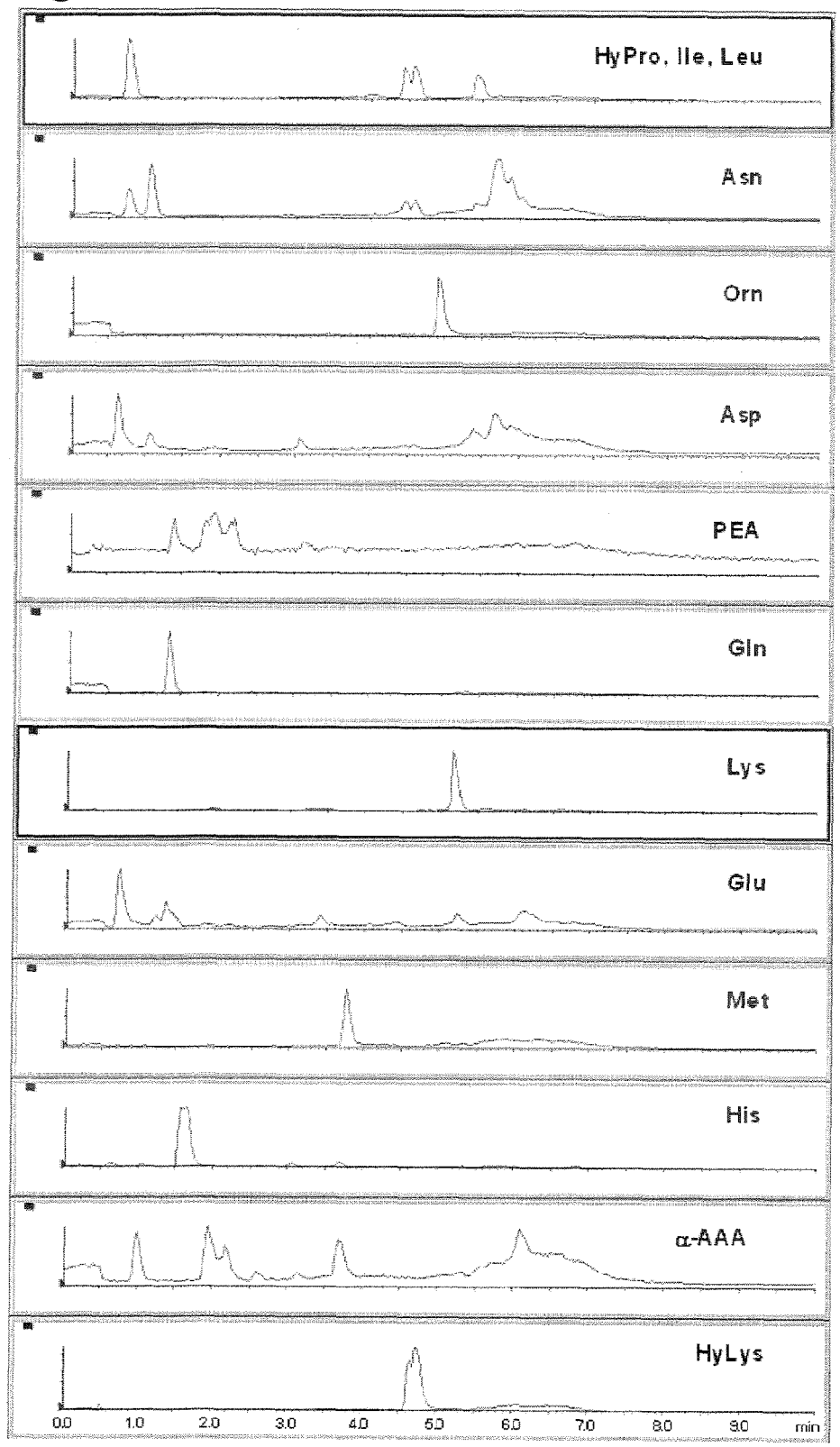
FIG. 8(b) shows a chromatogram depicting the results of the analysis of 39 kinds of compounds with amino group in Example 6: Analytical Example 5.
Figure 8C:
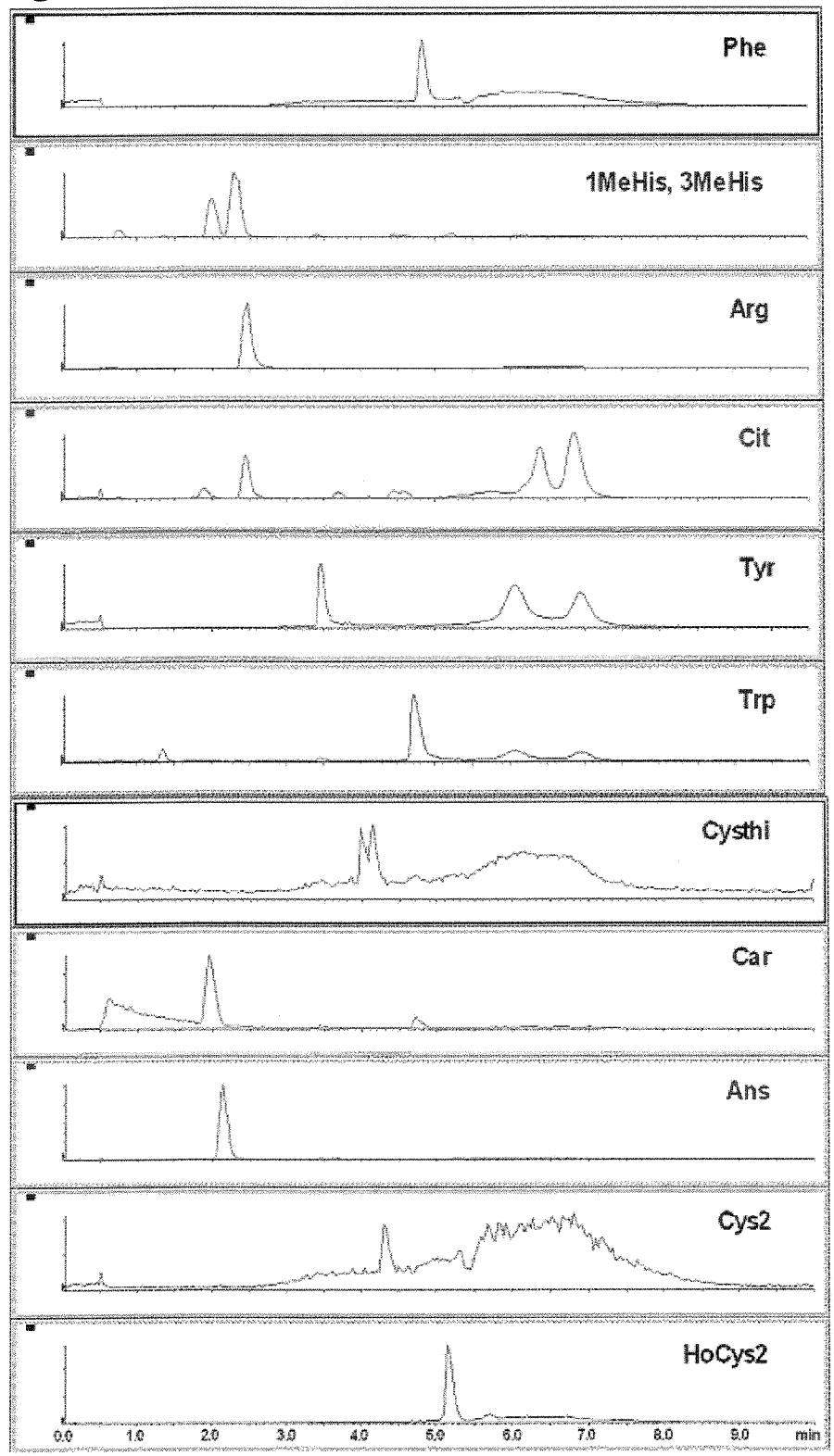
FIG. 8(c) shows a chromatogram depicting the results of the analysis of 39 kinds of compounds with amino group in Example 6: Analytical Example 5.

The analytical results are shown in FIG. 8. As in the above Analytical Examples 1 to 4, the individual 39 kinds of the compounds with amino group were separated and detected in about 6 minutes in this Analytical Example.

Example 7

Analytical Example 6

A mixture of 17 kinds of amino acid derivatives (a leucine derivative, an isoleucine derivative, a norleucine derivative, a sarcosine derivative, a β-alanine derivative, an alanine derivative, a γ-amino-n-butyric acid derivative, a β-aminoisobutyric acid derivative, an α-amino-n-butyric acid derivative, an α-aminoisobutyric acid derivative, a β-amino-n-butyric acid derivative, a 1-methylhistidine derivative, a 3-methylhistidine derivative, a homoserine derivative, a threonine derivative, a valine derivative and a norvaline derivative) as prepared with 3-aminopyridyl-N-hyroxysuccinimidylcarbamate (APDS) under the reaction conditions described above in the Example 1 were separated by reverse-phase HPLC, and then detected by selected reaction monitoring (positive mode). CAPCELL PAK AQ of a 2.0-mm inner diameter, a 50-mm length and a 3-μm particle diameter (Shiseido) was used as the separation column for reverse-phase HPLC at a flow rate of 0.3 mL/min under the following gradient conditions: time (ratio of mobile phase B) 0 to time 0.5-min (13%), time 0.51-min to time 4-min (50%), time 4.01-min to time 6-min (80%), and time 6.01-min to time 12-min (13%).

Figure 9:
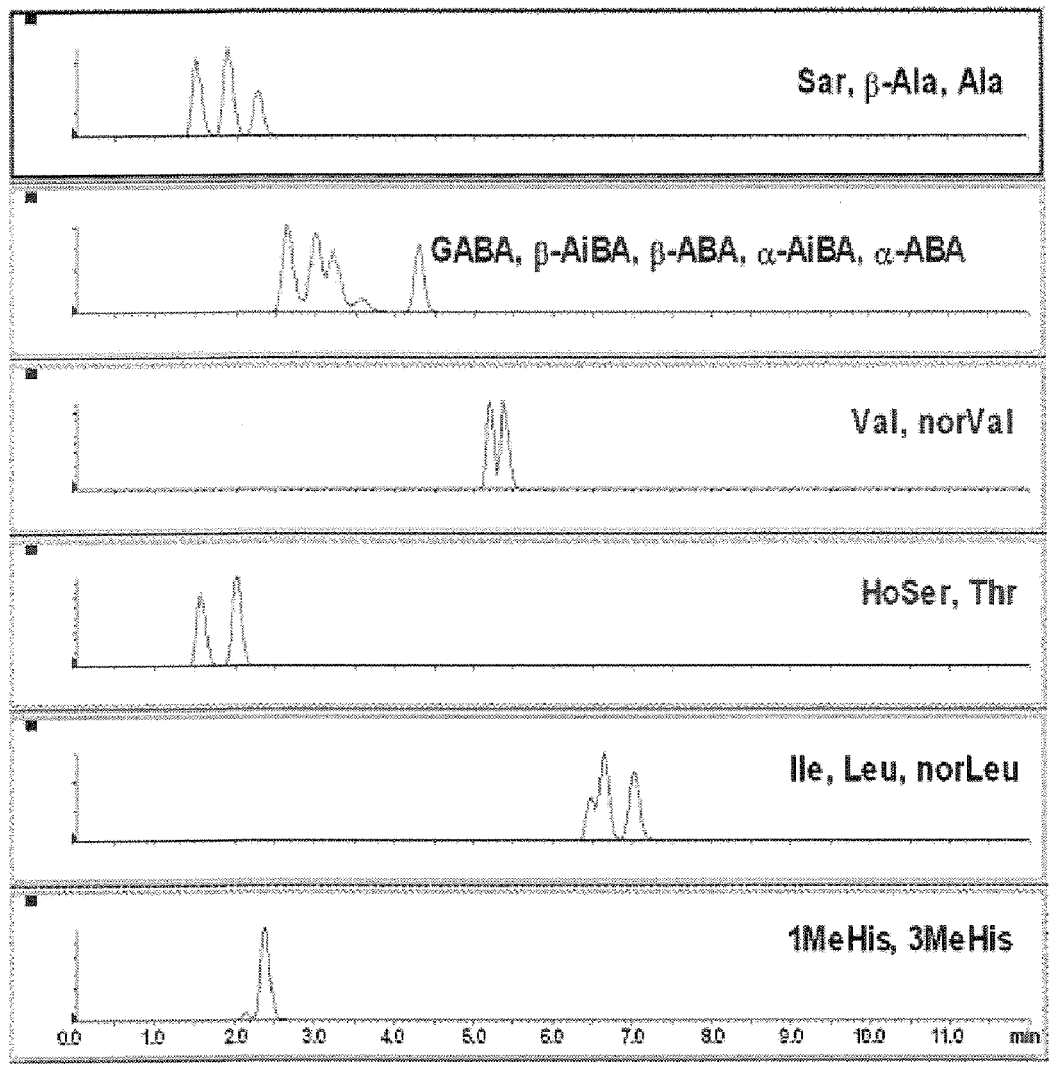
FIG. 9 shows a chromatogram depicting the results of the analysis of 17 kinds of compounds with amino group in Example 7: Analytical Example 6.
Figure 10A:
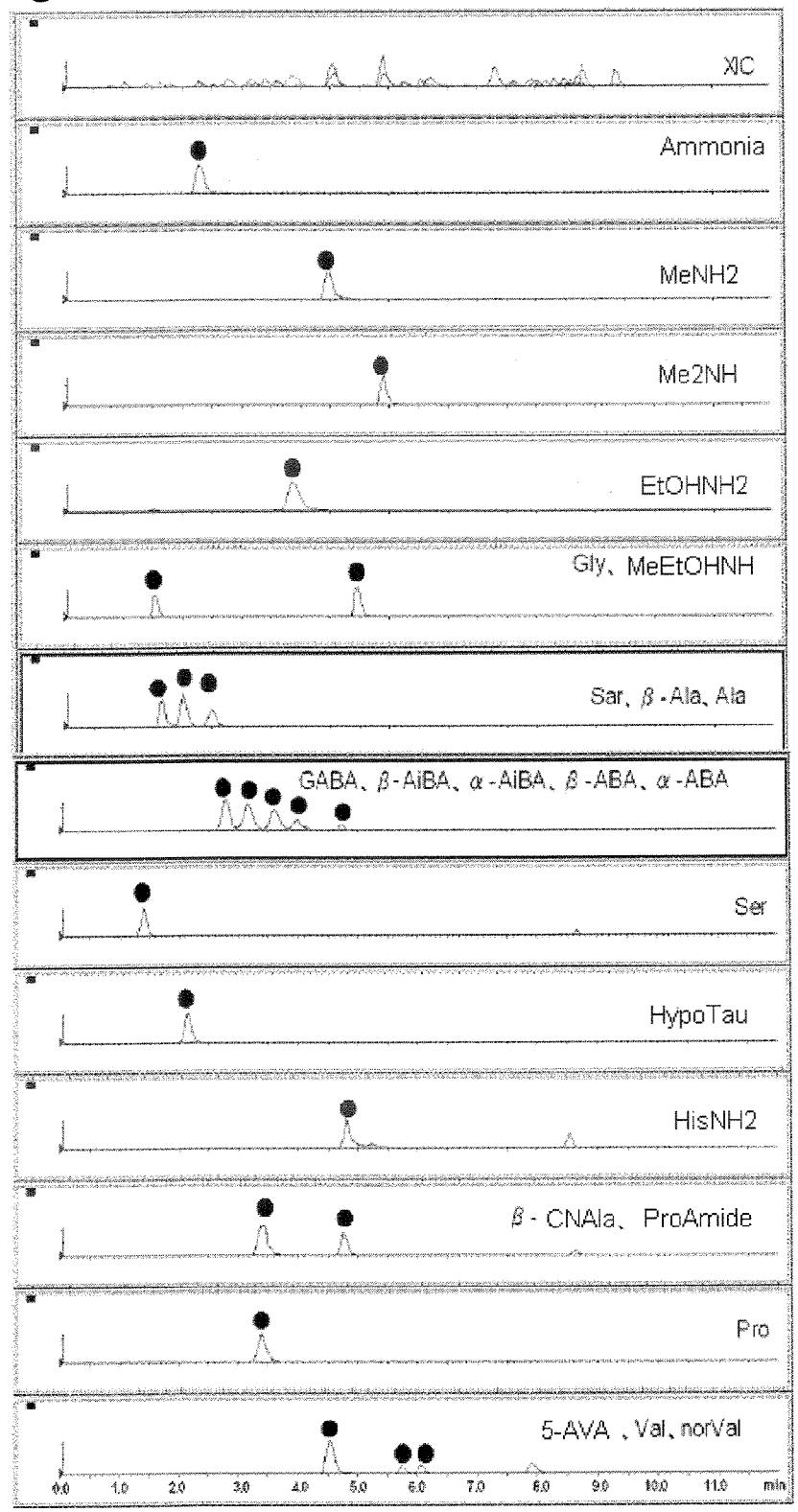
FIG. 10 (a) shows a chromatogram depicting the results of the analysis of 106 kinds of compounds with amino group in Example 9: Analytical Example 7.
FIG. 10(b) shows a chromatogram depicting the results of the analysis of 106 kinds of compounds with amino group in Example 9: Analytical Example 7.
FIG. 10(c) shows a chromatogram depicting the results of the analysis of 106 kinds of compounds with amino group in Example 9: Analytical Example 7.
FIG. 10(d) shows a chromatogram depicting the results of the analysis of 106 kinds of compounds with amino group in Example 9: Analytical Example 7.
FIG. 10(e) shows a chromatogram depicting the results of the analysis of 106 kinds of compounds with amino group in Example 9: Analytical Example 7.
Figure 10B:
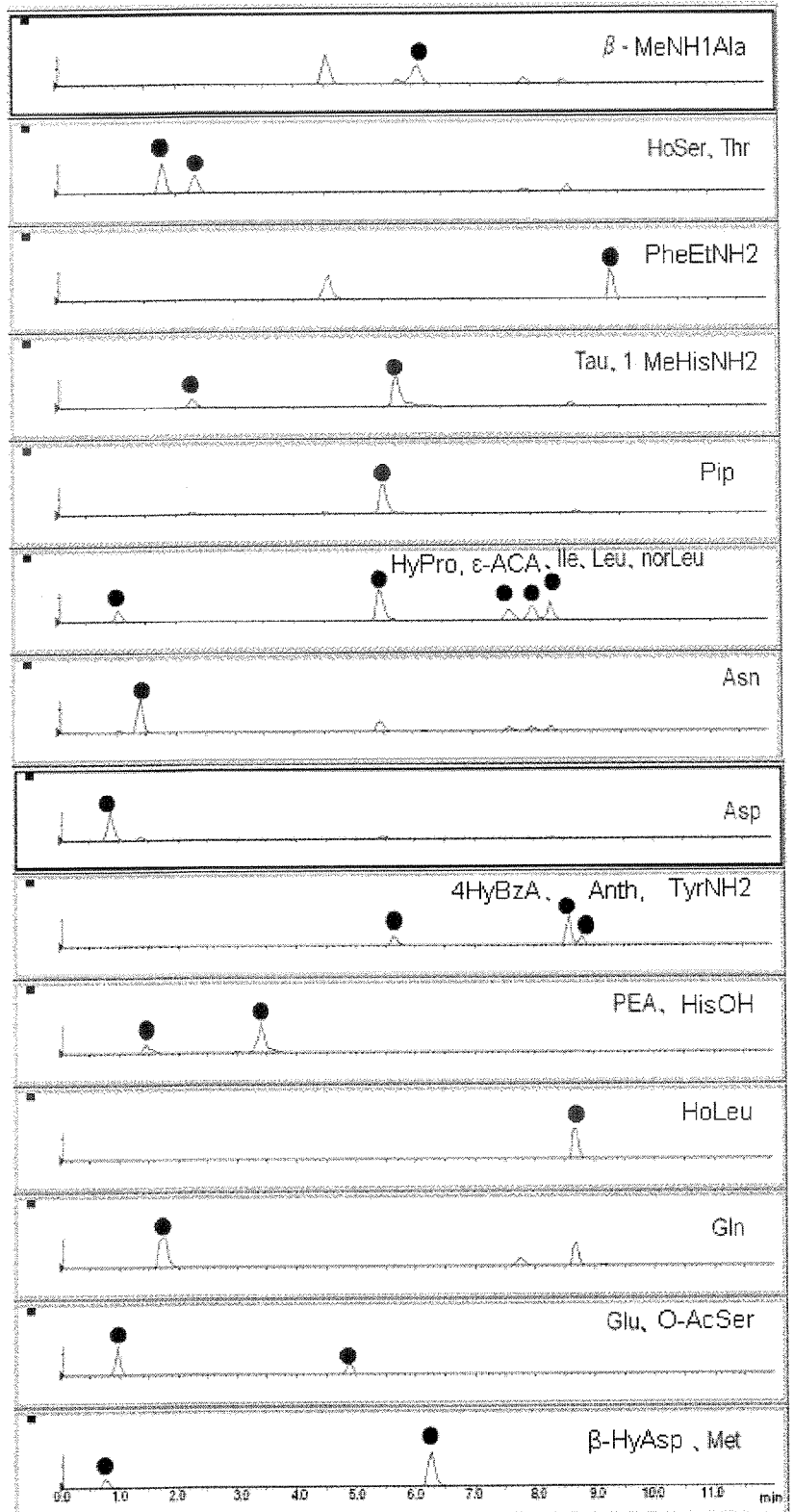
Figure 10C:
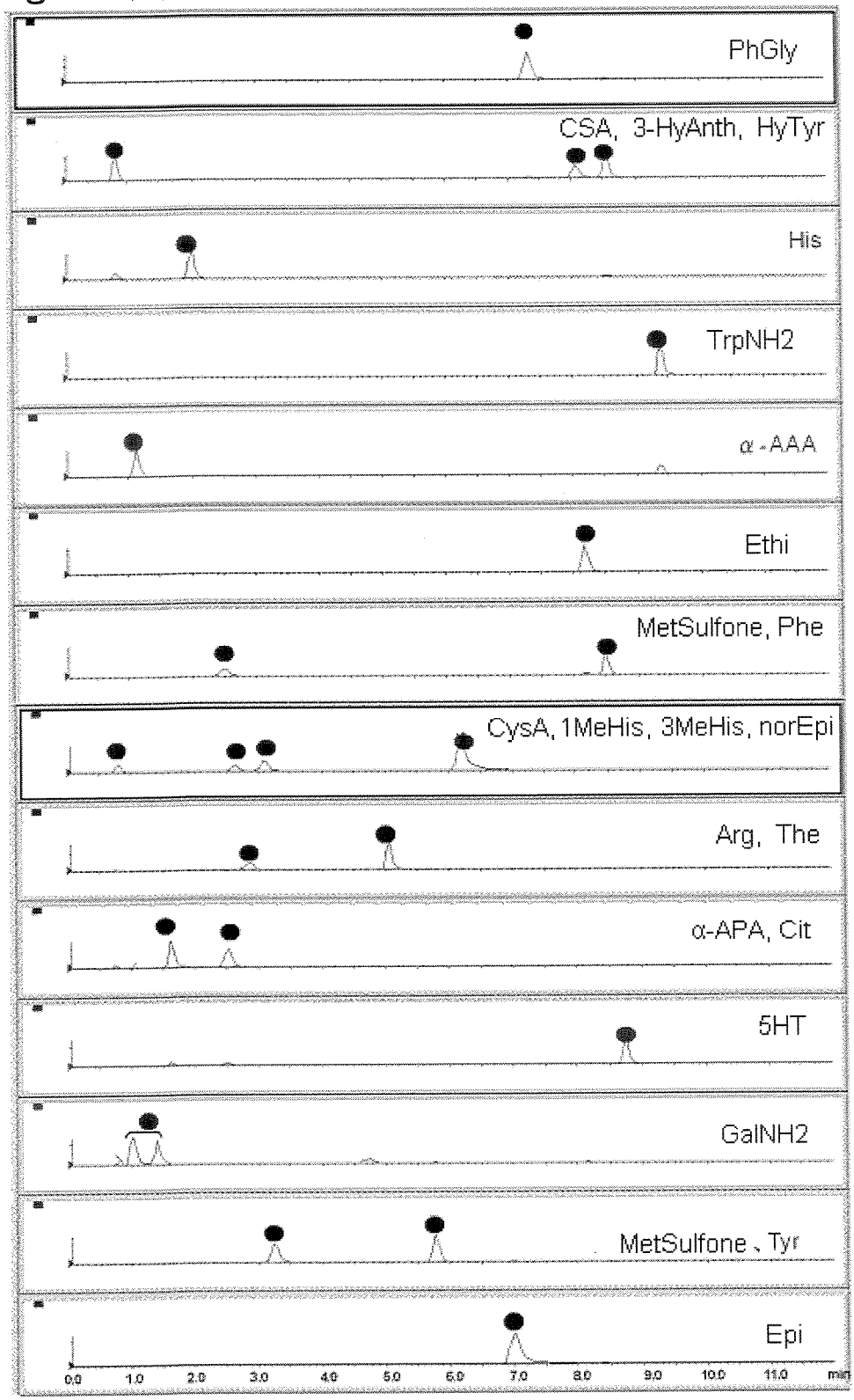
Figure 10D:
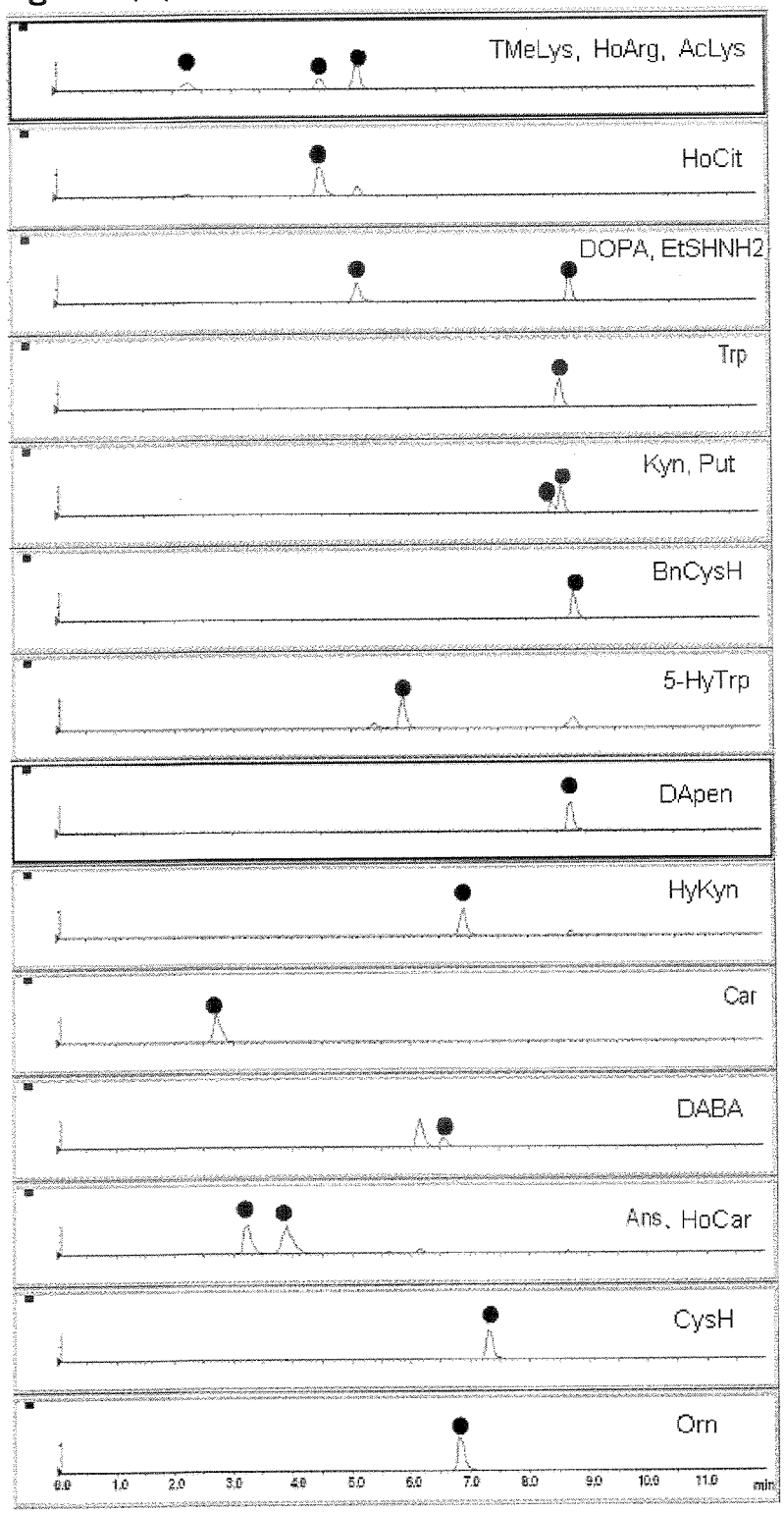
Figure 10E:
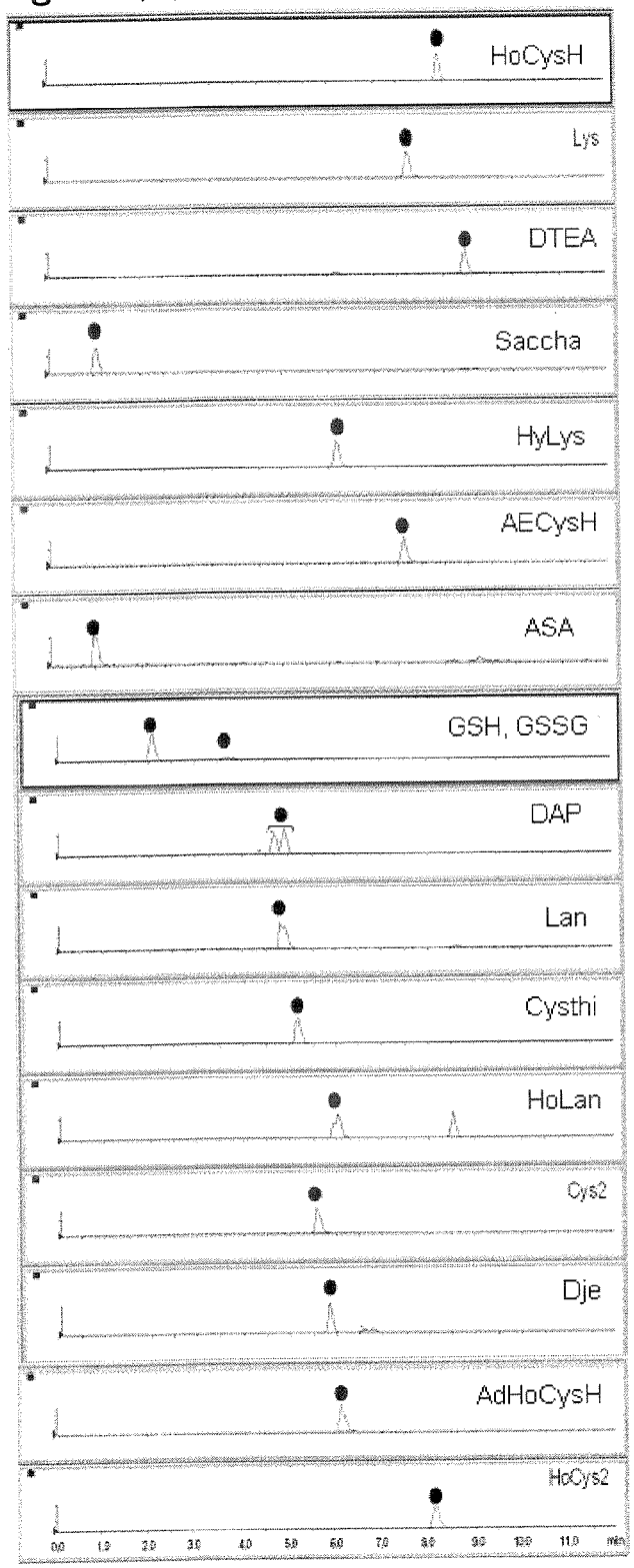

The analytical results are shown in FIG. 9. As shown in the individual charts in FIG. 9, the compounds with amino group having the same mass number, for example, the sarcosine derivative, the β-alanine derivative, and the alanine derivative can be separated and detected.

Example 8

Specific Procedure 2 for Derivatization of Compound with Amino Group

A 0.2 M borate buffer (pH 8.8) was added to 20 μl of a standard mix solution of compounds with amino group as a sample containing the compounds with amino group. 20 μl of a 3-aminopyridyl-N-hydroxysuccinimidylcarbamate reagent solution (10 mg of the reagent for derivatization in dissolution in 1 mL of acetonitrile for LC/MS) was added to the resulting mixture. The resulting mixture was heated at 55° C. for 10 minutes. After heating, the resulting mixture of the derivatives of the compounds with amino group was separated by reverse-phase liquid chromatography, and then introduced in a mass spectrometry apparatus. The mixture of the resulting derivatives of the compounds with amino group has been previously neutralized with 100 μl of aqueous 0.1% formic acid solution, to which 300 μL of the mobile phase A for liquid chromatography was added for dilution.

(1) Mobile phase A: an aqueous solution of 25 mM formic acid adjusted with aqueous ammonia to pH 6.0.
(2) Mobile phase B: a solution of acetonitrile mixed with distilled water at a ratio of 6:4.
(3) HPLC: Agilent HP 1100 series
(4) Detector: Mass spectrometry apparatus Sciex API 4000
(5) Temperature: 40° C.

Example 9

Analytical Example 7

A derivative mixture of 106 kinds of compounds with amino group as prepared with 3-aminopyridyl-N-hyroxysuccinimidylcarbamate (APDS) under the reaction conditions described above in the Example 8 were separated by reverse-phase HPLC, and then detected by selected reaction monitoring (positive mode). Inertsil C8-3 of a 2.1-mm inner diameter, a 50-mm length and a 3-μm particle diameter (GL Science) was used as the separation column for reverse-phase HPLC at a flow rate of 0.3 mL/min under the following gradient conditions: time (ratio of mobile phase B) 0 to time 1.25-min (4%), time 1.25-min to time 1.26-min (4% to 15%), time 1.26-min to time 5-min (15% to 20%), time 5-min to time 5.5-min (20% to 50%), time 5.5-min to time 6.5-min (50% to 95%), time 6.5-min to time 6.75-min (95%), and time 6.76-min to time 12-min (4%).

The analytical results are shown in FIG. 10. As apparently shown in FIG. 10, the individual 106 kinds of the compounds with amino group can be separated and detected in about 9 minutes.

Example 10

Analytical Example 8

A derivative mixture of 38 kinds of compounds with amino group as prepared with 3-aminopyridyl-N-hyroxysuccinimidylcarbamate (APDS) under the reaction conditions described above in the Example 8 were separated by reverse-phase HPLC, and then detected by selected ion monitoring (positive mode). Inertsil C8-3 of a 2.1-mm inner diameter, a 50-mm length and a 3-μm particle diameter (GL Science) was used as the separation column for reverse-phase HPLC at a flow rate of 0.3 mL/min under the following gradient conditions: time (ratio of mobile phase B) 0 to time 1.25-min (4%), time 1.25-min to time 1.26-min (4% to 15%), time 1.26-min to time 5-min (15% to 20%), time 5-min to time 5.5-min (20% to 50%), time 5.5-min to time 5.51-min (50% to 95%), time 5.51-min to time 6.5-min (95%), and time 6.51-min to time 12-min (4%).

Figure 11A:
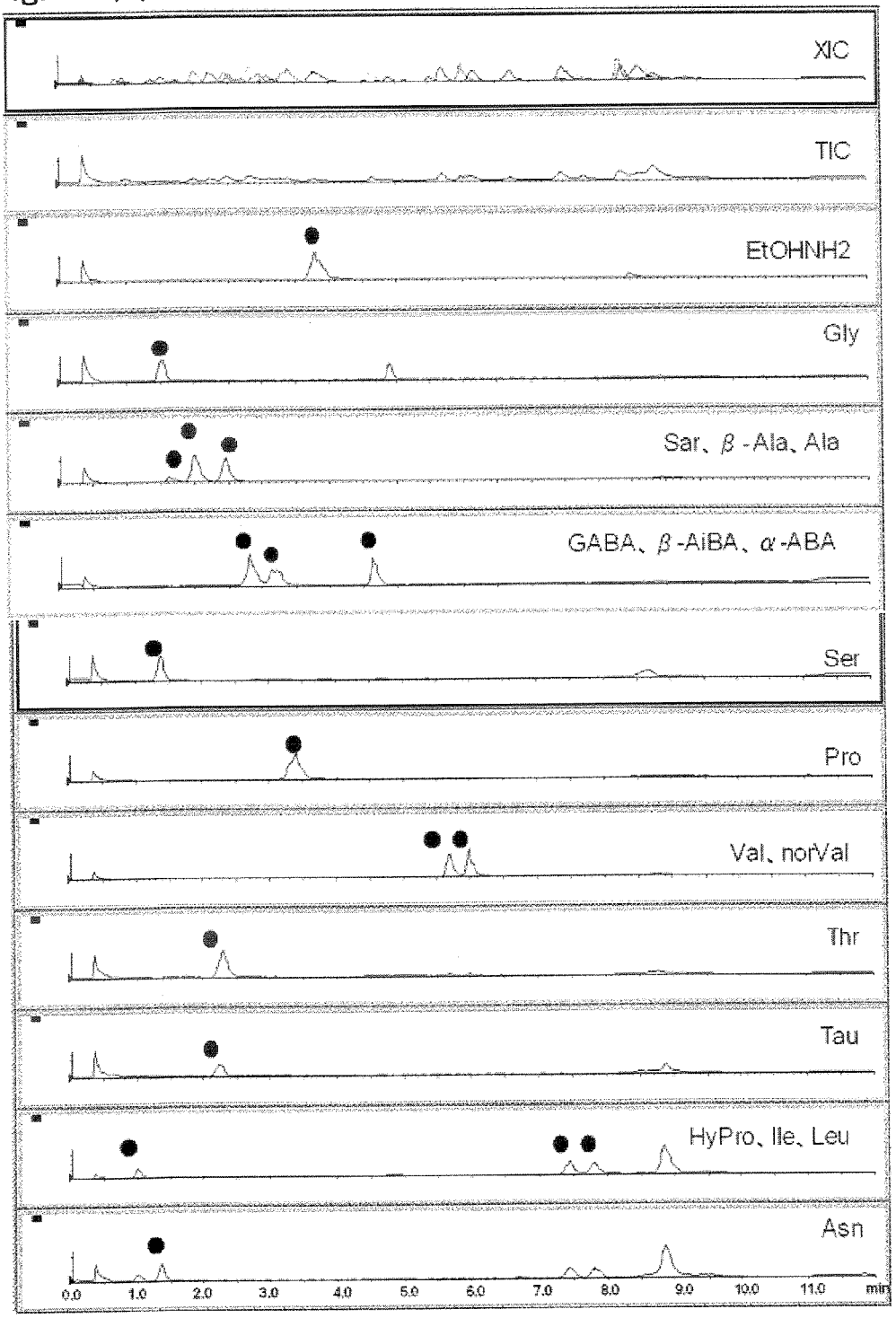
FIG. 11(a) shows a chromatogram depicting the results of the analysis of 38 kinds of compounds with amino group in Example 10: Analytical Example 8.
Figure 11B:
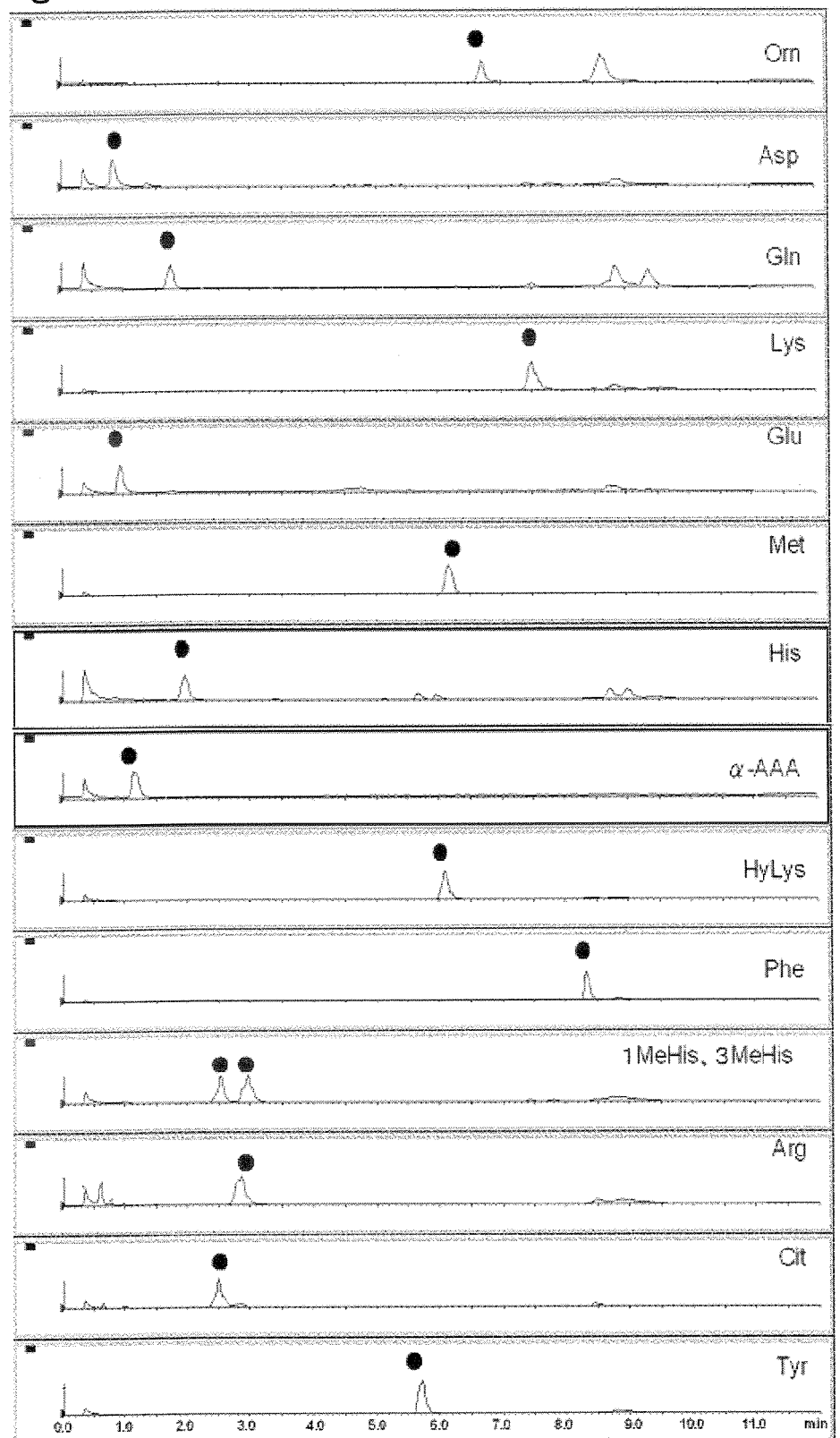
FIG. 11(b) shows a chromatogram depicting the results of the analysis of 38 kinds of compounds with amino group in Example 10: Analytical Example 8.
Figure 11C:
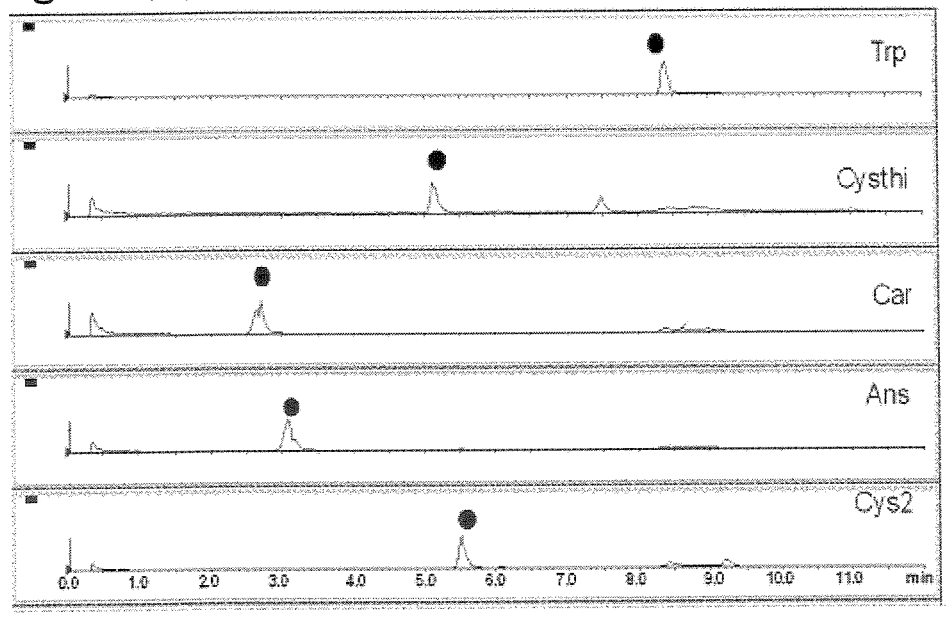
FIG. 11(c) shows a chromatogram depicting the results of the analysis of 38 kinds of compounds with amino group in Example 10: Analytical Example 8.

The analytical results are shown in FIG. 11. As apparently shown in FIG. 11, the individual 38 kinds of the compounds with amino group can be separated and detected in about 8 minutes.

Example 11

Specific Procedure 3 for Derivatization of Compound with Amino Group

A 0.2 M borate buffer (pH 8.8) was added to 20 μl of a standard mix solution of compounds with amino group as a sample containing the compounds with amino group. 20 μl of a 3-aminopyridyl-N-hydroxysuccinimidylcarbamate reagent solution (10 mg of the reagent for derivatization in dissolution in 1 mL of acetonitrile for LC/MS) was added to the resulting mixture. The resulting mixture of the derivatives of the compounds with amino group was heated at 55° C. for 10 minutes. After heating, the mixture with the derivative of the compounds with amino group was separated by reverse-phase liquid chromatography, and then introduced in a mass spectrometry apparatus. The mixture of the resulting derivatives of the compounds with amino group has been previously neutralized with 100 μl of aqueous 0.1% formic acid solution, to which 300 μL of the mobile phase A for liquid chromatography was added for dilution.

(1) Mobile phase A: aqueous 25 mM formic acid solution.
(2) Mobile phase B: a solution of acetonitrile mixed with distilled water at a ratio of 6:4.
(3) HPLC: Agilent HP 1100 series
(4) Detector: Mass spectrometry apparatus Sciex API 4000
(5) Temperature: 40° C.

Example 12

Analytical Example 9

A derivative mixture of 39 kinds of compounds with amino group as prepared with 3-aminopyridyl-N-hyroxysuccinimidylcarbamate (APDS) under the reaction conditions described above in the Example 111 were separated by reverse-phase HPLC, and then detected by selected reaction monitoring (positive mode). Atlantis dC18 of a 2.1-mm inner diameter, a 100-mm length and a 3-μm particle diameter (Waters) was used as the separation column for reverse-phase HPLC at a flow rate of 0.3 mL/min under the following gradient conditions: time (ratio of mobile phase B) 0 to time 0.5-min (0%), time 0.5-min to time 2.25-min (0% to 12%), time 2.25-min to time 2.26-min (12% to 18%), time 2.26-min to time 5.5-min (18% to 22%), time 5.5-min to time 6-min (22% to 50%), time 6-min to time 6.25-min (50% to 90%), time 6.25-min to time 6.5-min (90%) and time 6.51-min to time 12-min (0%).

Figure 12A:
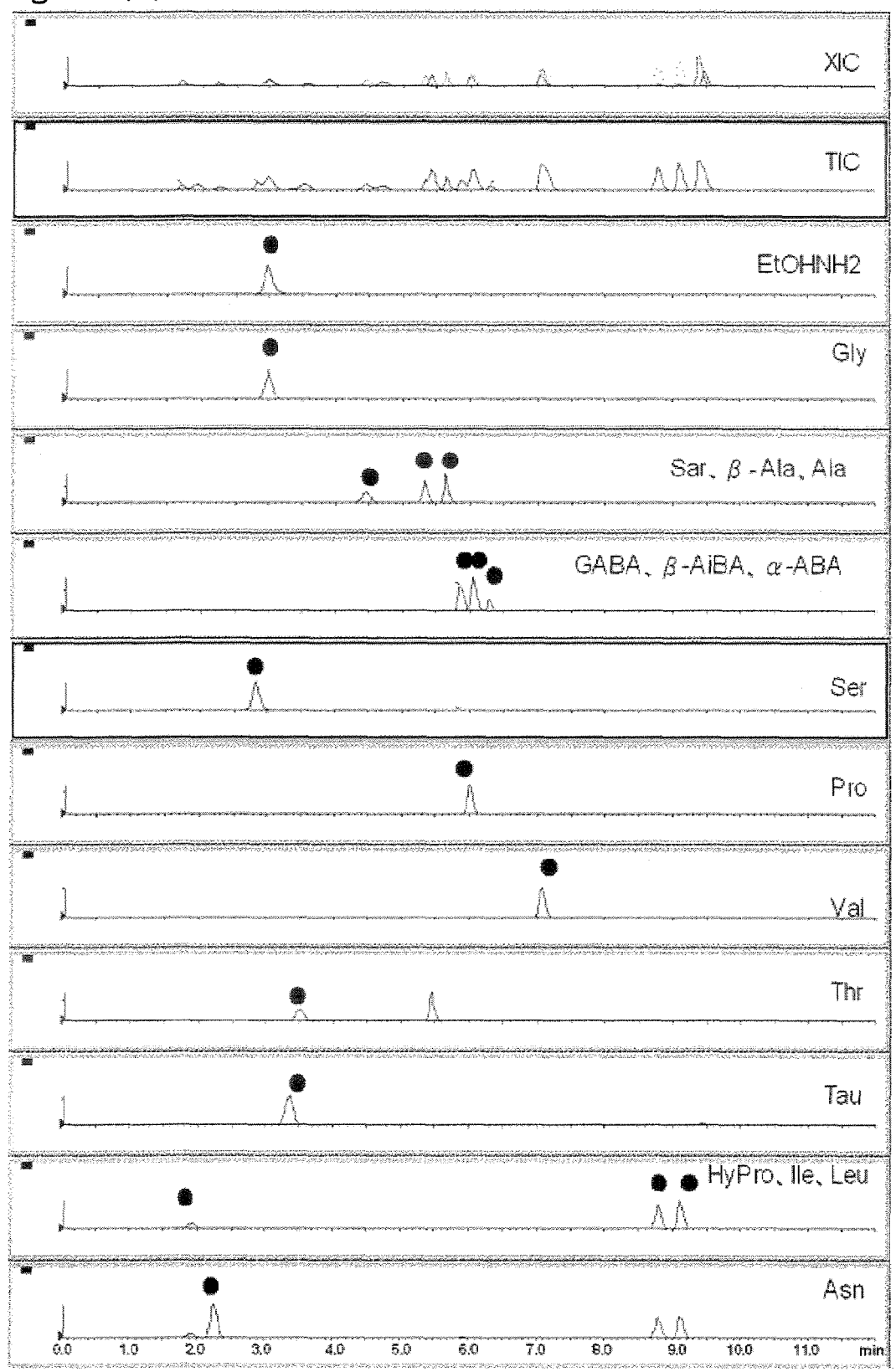
FIG. 12(a) shows a chromatogram depicting the results of the analysis of 39 kinds of compounds with amino group in Example 12: Analytical Example 9.
Figure 12B:
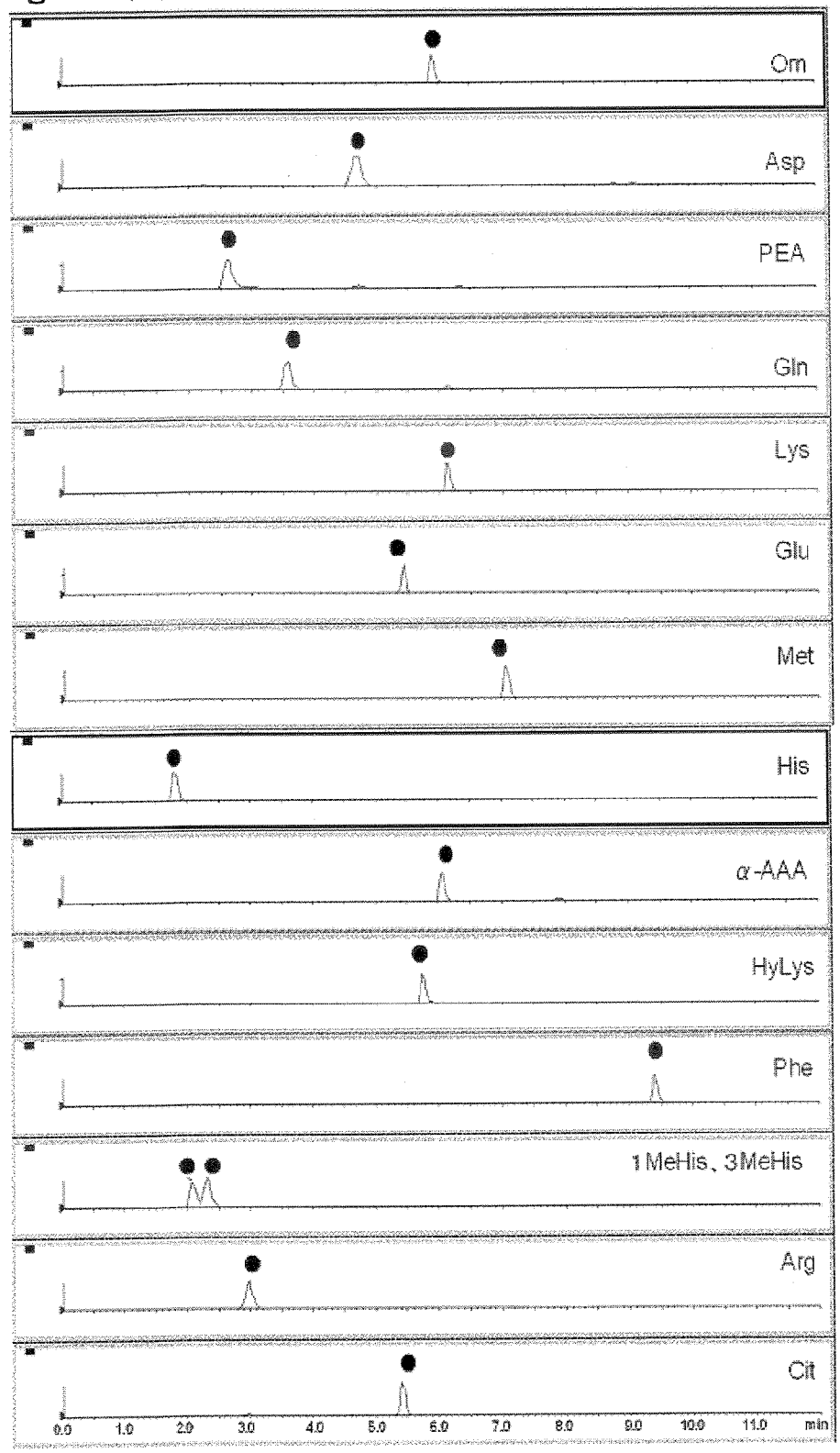
FIG. 12(b) shows a chromatogram depicting the results of the analysis of 39 kinds of compounds with amino group in Example 12: Analytical Example 9.
Figure 12C:
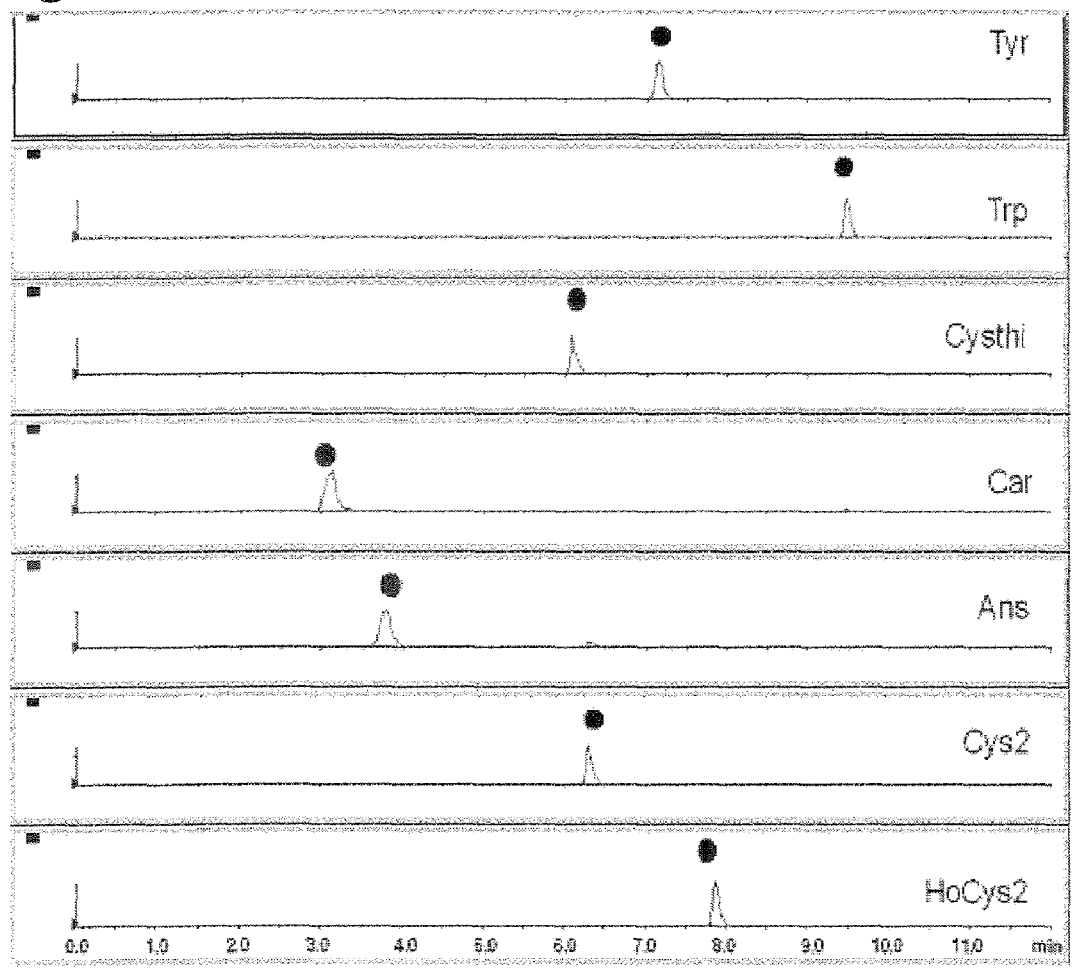
FIG. 12(c) shows a chromatogram depicting the results of the analysis of 39 kinds of compounds with amino group in Example 12: Analytical Example 9.

The analytical results are shown in FIG. 12. As shown in FIG. 12, the individual 39 kinds of the compounds with amino group can be separated and detected in about 10 minutes.

Numerous modifications and variations on the present invention are possible in light of the above teachings. It is, therefore, to be understood that within the scope of the accompanying claims, the invention may be practiced otherwise than as specifically described herein.

The invention claimed is:

1. A method for analyzing a compound with amino group comprising:
(a) reacting a compound with amino group contained in a sample comprising the same with a derivatization reagent to generate a derivatized compound, wherein said derivatized compound is a compound of formula (I) or formula (II):

wherein
$Ar_1$ denotes an optionally substituted hydrocarbon or a substituent comprising a carbocyclic or heterocyclic ring having an aromaticity, wherein the binding of $Ar_1$ to the nitrogen atom may be (i) the binding of a carbon ring or heterocyclic ring having an aromaticity directly to the nitrogen atom, (ii) the binding via a carbonyl group or an amide group to nitrogen atom, or (iii) the nitrogen atom may compose a part of a carbon ring or heterocyclic ring,
$R_1$ denotes a hydrogen atom, an optionally substituted alkyl group, or a ring forming carbon atom, and
$R_2$ denotes an optionally substituted alkyl group, and
wherein $Ar_1$ and $R_1$ or $R_1$ and $R_2$ may form a ring with each other,

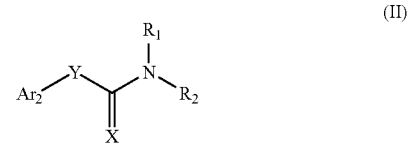

wherein
$Ar_2$ denotes a carbocyclic compound residue or a heterocyclic compound residue having an aromaticity,
X denotes an oxygen atom or a sulfur atom,
Y denotes an oxygen atom, a sulfur atom, a secondary amine, a tertiary amine, or an optionally substituted methylene group,
$R_1$ denotes a hydrogen atom, an optionally substituted alkyl group, or a ring forming carbon atom and
$R_2$ denotes an optionally substituted alkyl group, and
wherein $R_1$ and $R_2$ may form a ring with each other;
(b) eluting said derivatized compound by liquid chromatography via stepwise elution on a concentration gradient; and
(c) detecting said derivatized compound eluted from said liquid chromatography by mass spectrometry.

2. The method of claim 1, wherein said derivatization reagent is a substituted isocyanate aromatic compound, a substituted succinimidyl carbamate aromatic compound, a substituted carbamoyl halide aromatic compound, or a substituted carbamoyl alkoxy aromatic compound which is represented by formula (III) or formula (IV),

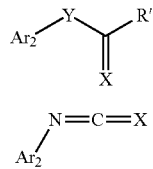

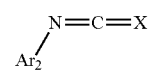

wherein
  Ar$_2$ denotes a carbocyclic compound residue or a heterocyclic compound residue having an aromaticity,
  R' denotes a fluorine atom, a chlorine atom, a bromine atom, an iodine atom, an N-hydroxysuccinimidyl group or an alkoxy group,
  X denotes an oxygen atom or a sulfur atom, and,
  Y denotes an oxygen atom, a sulfur atom, secondary amine, tertiary amine or an optionally substituted methylene group.

3. The method of claim 2, wherein said derivatization reagent is selected from the group consisting of phenylisocyanate, 3-pyridylisocyanate, phenylisothiocyanate, 3-pyridylisothiocyanate, phenyl-N-hydroxysuccinimidylcarbamate, 3-aminopyridyl-N-hydroxysuccinimidyl-carbamate, phenyl-N-hydroxythiosuccinimidyl-carbamate, and 3-pyridyl-N-hydroxythiosuccinimidyl-carbamate.

4. The method of claim 1, wherein said derivatized compound is a compound represented by formula (I),

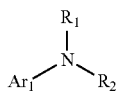

wherein
  Ar$_1$ denotes an optionally substituted hydrocarbon or a substituent comprising a carbocyclic or heterocyclic ring having an aromaticity, wherein the binding of Ar$_1$ to the nitrogen atom may be (i) the binding of a carbon ring or heterocyclic ring having an aromaticity directly to the nitrogen atom, (ii) the binding via a carbonyl group or an amide group to nitrogen atom, or (iii) the nitrogen atom may compose a part of a carbon ring or heterocyclic ring,
  R$_1$ denotes a hydrogen atom, an optionally substituted alkyl group, or a ring forming carbon atom, and
  R$_2$ denotes an optionally substituted alkyl group, and
  wherein Ar$_1$ and R$_1$ or R$_1$ and R$_2$ may form a ring with each other.

5. The method of claim 4, wherein said derivatization reagent is a substituted isocyanate aromatic compound, a substituted succinimidyl carbamate aromatic compound, a substituted carbamoyl halide aromatic compound, or a substituted carbamoyl alkoxy aromatic compound which is represented by formula (III) or formula (IV),

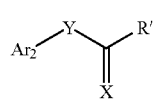

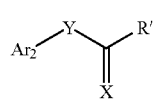

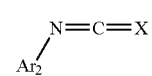

wherein
  Ar$_2$ denotes a carbocyclic compound residue or a heterocyclic compound residue having an aromaticity,
  R' denotes a fluorine atom, a chlorine atom, a bromine atom, an iodine atom, an N-hydroxysuccinimidyl group or an alkoxy group,
  X denotes an oxygen atom or a sulfur atom, and,
  Y denotes an oxygen atom, a sulfur atom, secondary amine, tertiary amine or an optionally substituted methylene group.

6. The method of claim 5, wherein said derivatization reagent is selected from the group consisting of phenylisocyanate, 3-pyridylisocyanate, phenylisothiocyanate, 3-pyridylisothiocyanate, phenyl-N-hydroxysuccinimidylcarbamate, 3-aminopyridyl-N-hydroxy-succinimidylcarbamate, phenyl-N-hydroxythiosuccinimidyl-carbamate, and 3-pyridyl-N-hydroxythiosuccinimidyl-carbamate.

7. The method of claim 1, wherein said derivatized compound is a compound represented by formula (II),

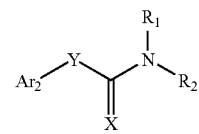

wherein Ar$_2$ denotes a carbocyclic compound residue or a heterocyclic compound residue having an aromaticity, X denotes an oxygen atom or a sulfur atom, Y denotes an oxygen atom, a sulfur atom, a secondary amine, a tertiary amine, or an optionally substituted methylene group, R$_1$ denotes a hydrogen atom, an optionally substituted alkyl group, or a ring forming carbon atom and R$_2$ denotes an optionally substituted alkyl group, where R$_1$ and R$_2$ may form a ring with each other.

8. The method of claim 7, wherein said derivatization reagent is a substituted isocyanate aromatic compound, a substituted succinimidyl carbamate aromatic compound, a substituted carbamoyl halide aromatic compound, or a substituted carbamoyl alkoxy aromatic compound which is represented by formula (III) or formula (IV),

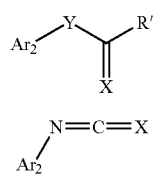

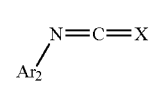

wherein
  Ar$_2$ denotes a carbocyclic compound residue or a heterocyclic compound residue having an aromaticity,
  R' denotes a fluorine atom, a chlorine atom, a bromine atom, an iodine atom, an N-hydroxysuccinimidyl group or an alkoxy group,
  X denotes an oxygen atom or a sulfur atom, and, Y denotes an oxygen atom, a sulfur atom, secondary amine, tertiary amine or an optionally substituted methylene group.

9. The method of claim 8, wherein said derivatization reagent is selected from the group consisting of phenylisocyanate, 3-pyridylisocyanate, phenylisothiocyanate, 3-pyridyl-isothiocyanate, phenyl-N-hydroxysuccinimidylcarbamate, 3-aminopyridyl-N-hydroxy-succinimidylcarbamate, phenyl-N-hydroxythiosuccinimidyl-carbamate, and 3-pyridyl-N-hydroxythiosuccinimidyl-carbamate.

10. The method of claim 1, wherein said derivatized compound is a compound with phenylcarbamylamino group, a compound with 3-pyridyl-carbamylamino group, a compound with phenylthiocarbamylamino group, a compound with 3-pyridylthiocarbamylamino group, a compound with p-trimethylammoniumanilylcarbamylamino group, or a compound with p -dimethylammoniumanilylcarbamylamino group.

11. The method of claim 1, wherein said compound with amino group is at least one compound selected from the group consisting of asparagine, aspartic acid, O-acetylserine, Nα-acetyllysine, S-adenosylhomocysteine, S-aminoethyl cysteine, ε-amino-n-caproic acid, α-amino adipic acid, 4-aminobenzoic acid, α-aminoisobutyric acid, β-aminoisobutyric acid, 5-aminovaleric acid, α-aminopimelic acid, α-amino-n-butyric acid, β-amino-n-butyric acid, γ-amino-n-butyric acid, β-alanine, alanine, argininosuccinic acid, arginine, anserine, anthranilic acid, isoleucine, ethanolamine, ethionine, epinephrine, ornithine, galactosamine, carnosine, kynurenine, glycine, reduced glutathione, oxidized glutathione, glutamine, glutamic acid, Saccharopine, sarcosine, β-cyanoalanine, α,ε-diaminopimelic acid, 1,5-diaminopentane, α,γ-diaminobutyric acid, djenkolic acid, cystathionine, cystamine, cystine, cysteamine, cysteine, cysteic acid, cysteine sulfinic acid, citrulline, dihydroxy-phenylalanine, dimethylamine, threonine, serine, taurine, tyramine, tyrosine, theanine, tryptamine, tryptophan, Nε,Nε,Nε-trimethyllysine, norepinephrine, norvaline, norleucine, valine, histamine, histidinol, histidine, β-hydroxyaspartic acid, 3-hydroxyanthranilic acid, 3-hydroxykynurenine, hydroxy tyramine, 5-hydroxytryptamine, 5-hydroxytryptophan, hydroxyproline, hydroxylysine, pipecolic acid, hypotaurine, phenylalanine, 2-phenylethylamine, phenylglycine, putrescine, proline, prolinamide, S-benzil cysteine, O-phosphoethanolamine, homoarginine, homocamosine, homocystine, homocysteine, homocitrulline, homoserine, homolanthionine, homoleucine, methionine, methionine sulphoxide, methionine sulfone, β-N-methylamino alanine, methylamine, 1-methylhistamine, 1-methylhistidine, 3-methylhistidine, monomethyl ethanolamine, lanthionine, lysine and leucine.

12. The method of claim 1, wherein said eluting conducted in a mode, wherein the difference in elution time between a derivatized compound having the shortest elution time among a histidine derivative, aspartic acid derivative, arginine derivative, hydroxyproline derivative, glutamic acid derivative, argininosuccinic acid derivative, cysteine sulfinic acid derivative, cysteic acid derivative and β-hydroxyaspartic acid derivative, and a derivatized compound having the longest elution time among a tryptophan derivative, lysine derivative, phenylalanine derivative, 1,5-diaminopentane derivative, homoleucine derivative, tryptamine derivative, homolanthionine derivative, tyramine derivative, cysteamine derivative, putrescine derivative, cystamine derivative and 2-phenylethylamine derivative is from 3 to 20 minutes.

13. The method of claim 1, wherein said detecting individually selects and detects individually two or more derivatized compounds selected from the following group (a), and two or more derivatized compounds selected from at least one of the groups (b) to (f):

(a) ε-amino-n-caproic acid, a leucine derivative, an isoleucine derivative, and a norleucine derivative, (b) a sarcosine derivative, a β-alanine derivative, and an alanine derivative, (c) a γ-amino-n-butyric acid derivative, a β-aminoisobutyric acid derivative, an α-amino-n-butyric acid derivative, an α-aminoisobutyric acid derivative and a β-amino-n-butyric acid derivative, (d) a 1-methylhistidine derivative and a 3-methylhistidine derivative, (e) a homoserine derivative, and a threonine derivative, (f) a 5-aminovaleric acid derivative, a valine derivative and a norvaline derivative, (g) a 4-hydroxybenzoic acid derivative and an anthranilic acid derivative, (h) a glutamic acid derivative and an O-acetylserine derivative, and (i) an anserine derivative and a homocamosine derivative.

14. The method of claim 1, wherein said detecting comprises (a) ionizing said derivatized compound by a method selected from the group consisting of electro-spray ionization, atmospheric pressure chemical ionization, and matrix-assisted laser desorption ionization, and sonic spray ionization, and (b) separating ions by at least one mechanism selected from the group consisting magnetic field, electric field, ion trap, time of flight, quadrupole, and Fourier transform cyclotron.

* * * * *